United States Patent
Webler et al.

(10) Patent No.: US 7,736,301 B1
(45) Date of Patent: Jun. 15, 2010

(54) ROTATABLE FERRULES AND INTERFACES FOR USE WITH AN OPTICAL GUIDEWIRE

(75) Inventors: William E. Webler, Escondido, CA (US); Andrej M. Chudy, Temecula, CA (US); Marc M. Jalisi, Weston, FL (US); Kevin M. Phillips, Temecula, CA (US); Michael D. Whitt, Carlsbad, CA (US); Susan Norton, Bonsall, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1029 days.

(21) Appl. No.: 10/025,515

(22) Filed: Dec. 18, 2001

(51) Int. Cl.
*A61B 1/07* (2006.01)
*G02B 6/36* (2006.01)

(52) U.S. Cl. .................. 600/125; 600/136; 600/137; 385/53; 385/88; 385/92

(58) Field of Classification Search ............ 385/53–55, 385/60, 68, 72, 76–85, 88–94; 600/114, 600/125, 136–138; 606/15–18
See application file for complete search history.

(56) References Cited

U.S. PATENT DOCUMENTS

| 4,624,243 | A | * | 11/1986 | Lowery et al. | 600/136 |
|---|---|---|---|---|---|
| 4,762,120 | A | * | 8/1988 | Hussein | 600/136 |
| 4,900,122 | A | * | 2/1990 | Frank et al. | 385/88 |
| 4,979,498 | A | * | 12/1990 | Oneda et al. | 600/118 |
| 5,152,277 | A | * | 10/1992 | Honda et al. | 600/116 |
| 5,188,093 | A | * | 2/1993 | Lafferty et al. | 600/109 |
| 5,300,067 | A | * | 4/1994 | Nakajima et al. | 606/16 |
| 5,321,501 | A | | 6/1994 | Swanson et al. | 356/345 |
| 5,396,880 | A | * | 3/1995 | Kagan et al. | 600/109 |
| 5,407,443 | A | * | 4/1995 | Kobayashi et al. | 606/3 |
| 5,459,570 | A | | 10/1995 | Swanson et al. | 356/345 |
| 5,863,287 | A | * | 1/1999 | Segawa | 600/121 |
| 5,872,879 | A | | 2/1999 | Hamm | |
| 5,935,075 | A | | 8/1999 | Casscells et al. | 600/474 |
| RE36,434 | E | * | 12/1999 | Hamlin et al. | 600/109 |
| 6,022,150 | A | * | 2/2000 | Erdman et al. | 385/81 |
| 6,111,645 | A | | 8/2000 | Tearney et al. | 356/354 |
| 6,134,003 | A | | 10/2000 | Tearney et al. | 356/345 |
| 6,263,133 | B1 | * | 7/2001 | Hamm | 385/33 |
| 6,350,231 | B1 | * | 2/2002 | Ailinger et al. | 600/121 |

(Continued)

OTHER PUBLICATIONS

Brazinski et al., "Optical Coherence Tomography for Optical Biopsy" Circulation 93(6):1206-1213 (Mar. 1996).

(Continued)

*Primary Examiner*—John P Leubecker
(74) *Attorney, Agent, or Firm*—Fulwider Patton LLP

(57) ABSTRACT

Devices and methods for passing optical radiation into and out of a body lumen which can include a rotatable ferrule for use in an optical guidewire and methods for using a rotation ferrule. The rotatable ferrule may be either rotatably captured by and free to rotate within a guidewire, or may rotate upon release from a releasable, mechanically stable friction-fit engagement with a guidewire. Sterile interfaces for readily connecting and disconnecting an optical guidewire with and from other optical instrumentation while maintaining the sterility of the guidewire are provided as well as methods for using a sterile interface device. Interface devices can provide either direct or indirect optical and mechanical connection between an optical guidewire and peripheral instrumentation.

2 Claims, 9 Drawing Sheets

U.S. PATENT DOCUMENTS

| | | | |
|---|---|---|---|
| 6,445,939 B1 * | 9/2002 | Swanson et al. | 600/342 |
| 6,461,349 B1 * | 10/2002 | Elbrecht et al. | 606/16 |
| 6,626,582 B2 * | 9/2003 | Farrar et al. | 385/53 |
| 6,687,010 B1 * | 2/2004 | Horii et al. | 356/479 |
| 6,761,684 B1 * | 7/2004 | Speier | 600/121 |
| 2002/0064328 A1 * | 5/2002 | Neuberger et al. | 385/1 |

OTHER PUBLICATIONS

Brazinski et al., "Assessing atherosclerotic plaque morphology: comparison of optical coherence tomography and high frequency intravascular ultrasound" Heart 77:397-403 (1997).

Brezinski et al., "Optical Biopsy with Optical Coherence Tomography: Feasibility for Surgical Diagnostics" Journal of Surgical Research 71:32-40 (1997).

Fujimoto et al., "New Technology for High-Speed and High-Resolution Optical Coherence Tomography" Annals New York Academy of Sciences 95-107.

Tearney et al., "Scanning single-mode fiber optic catheter-endoscope for optical coherence tomography" Optics Letters 21(7):543-545 (Apr. 1996).

* cited by examiner

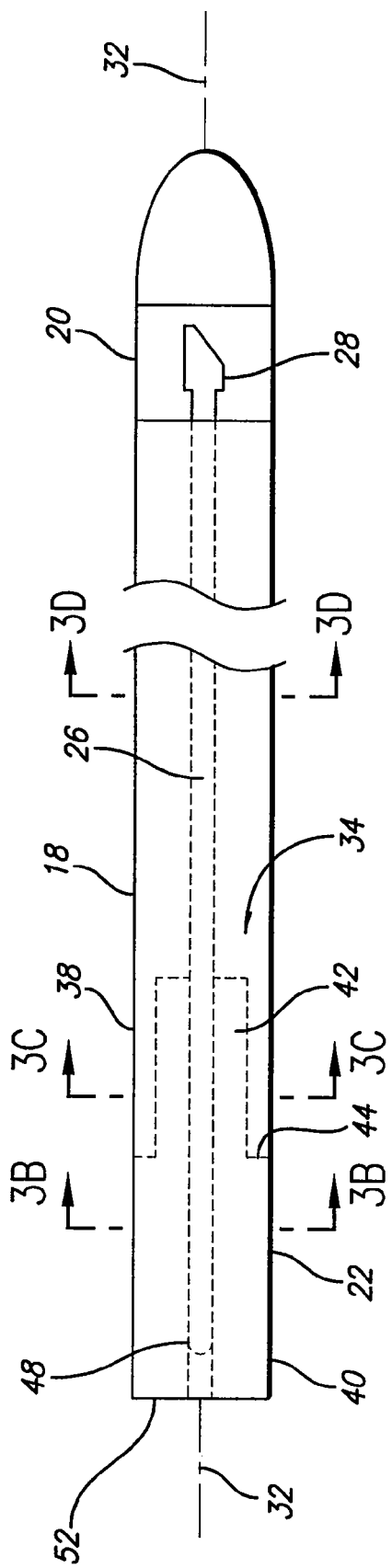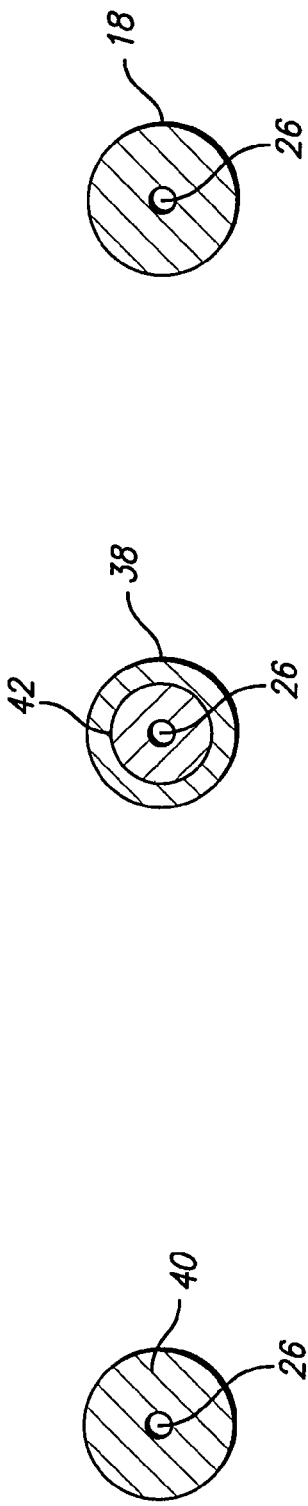

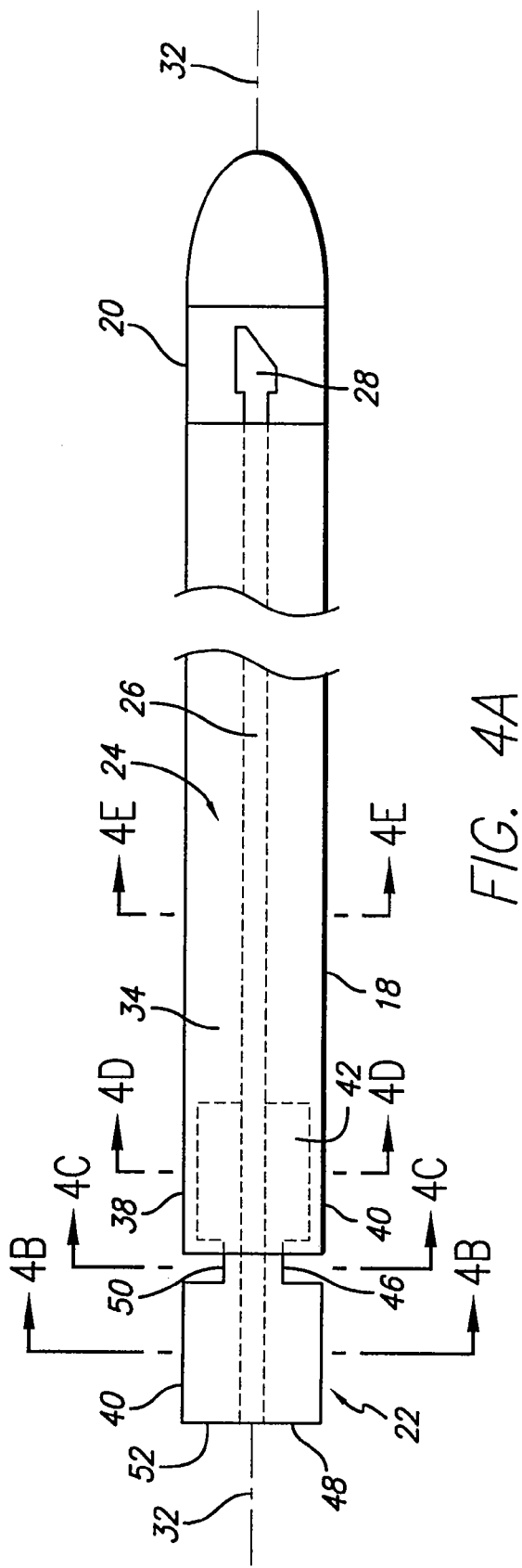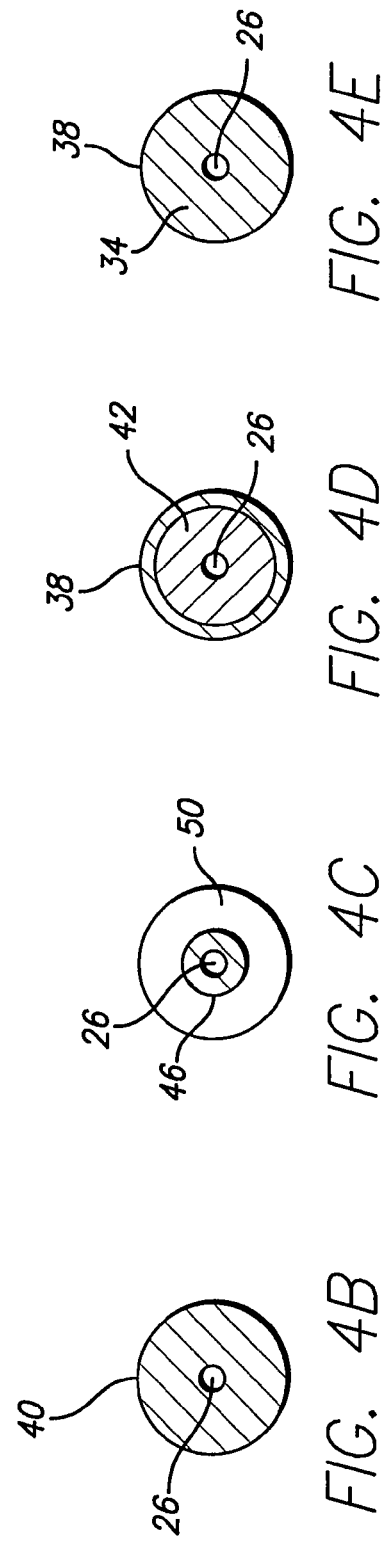

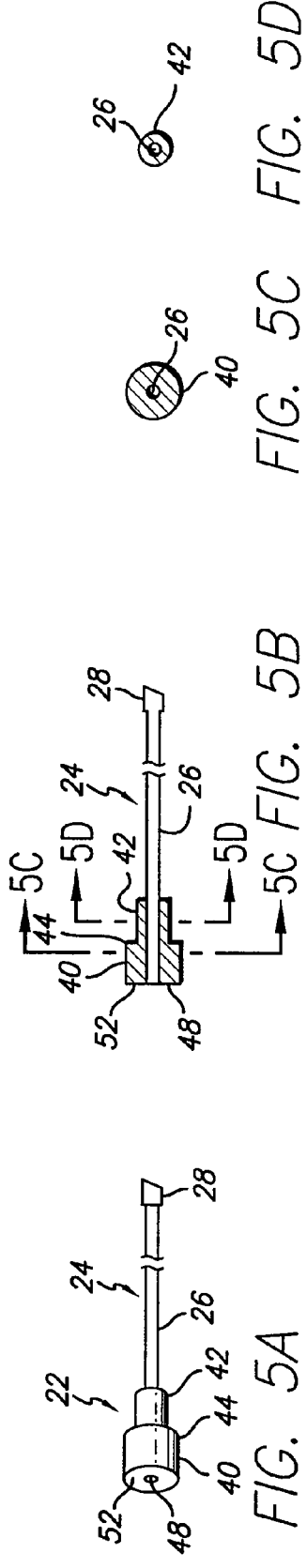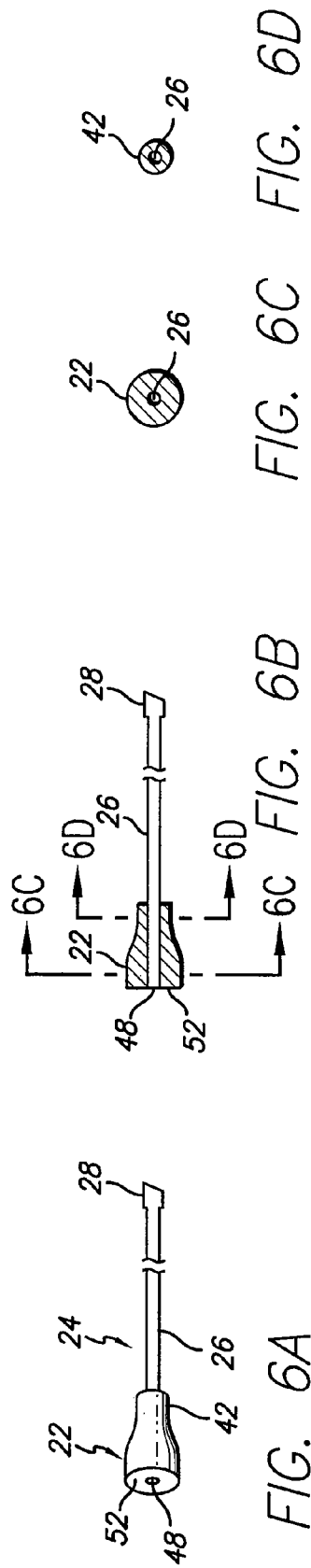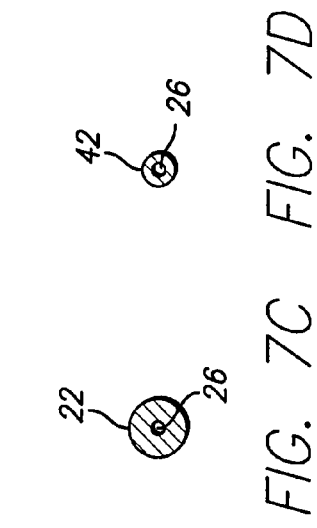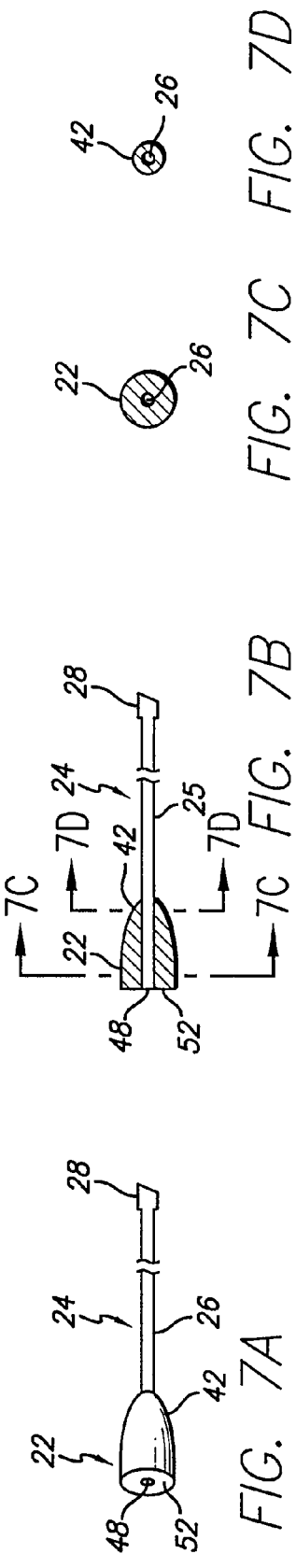

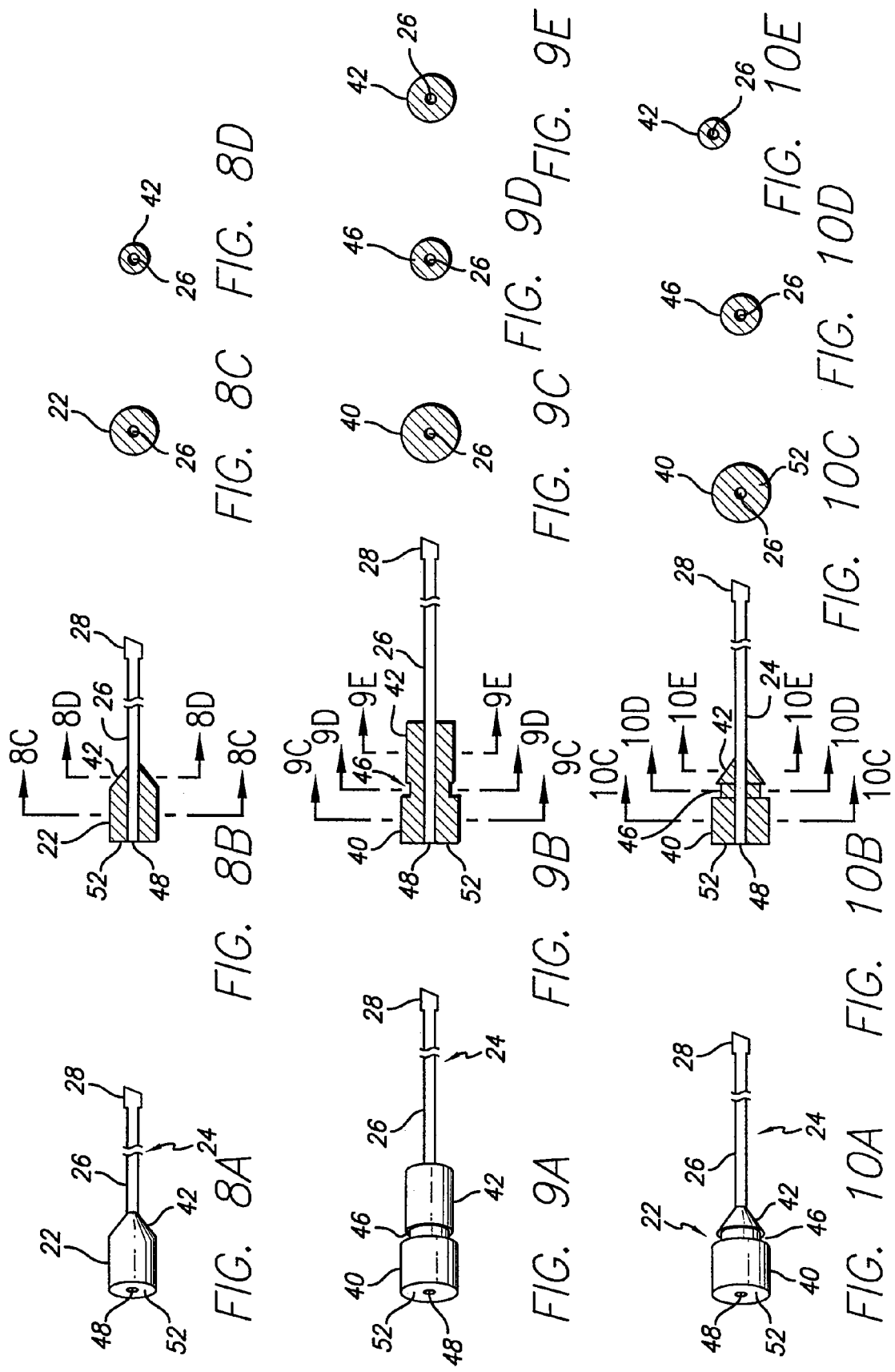

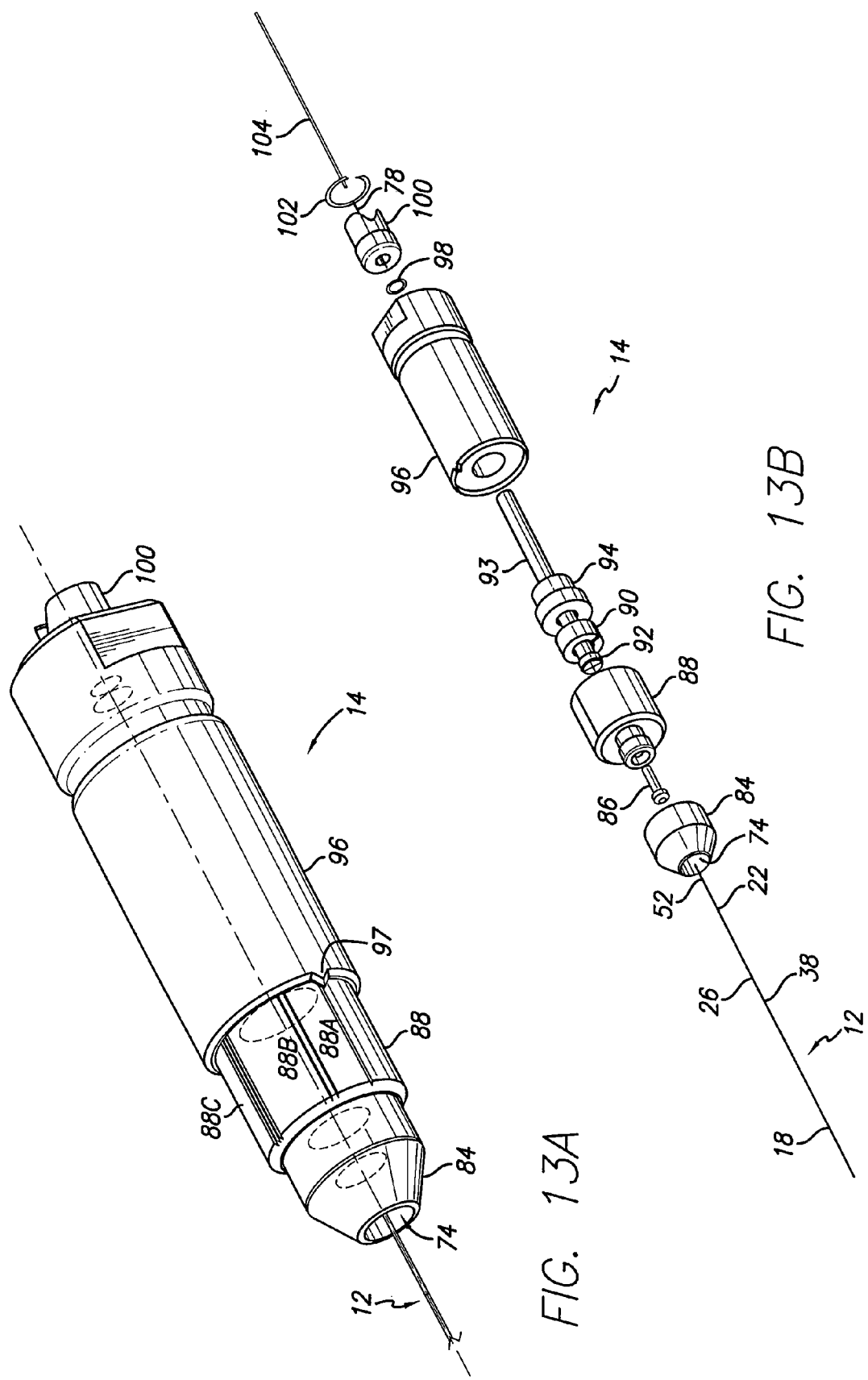

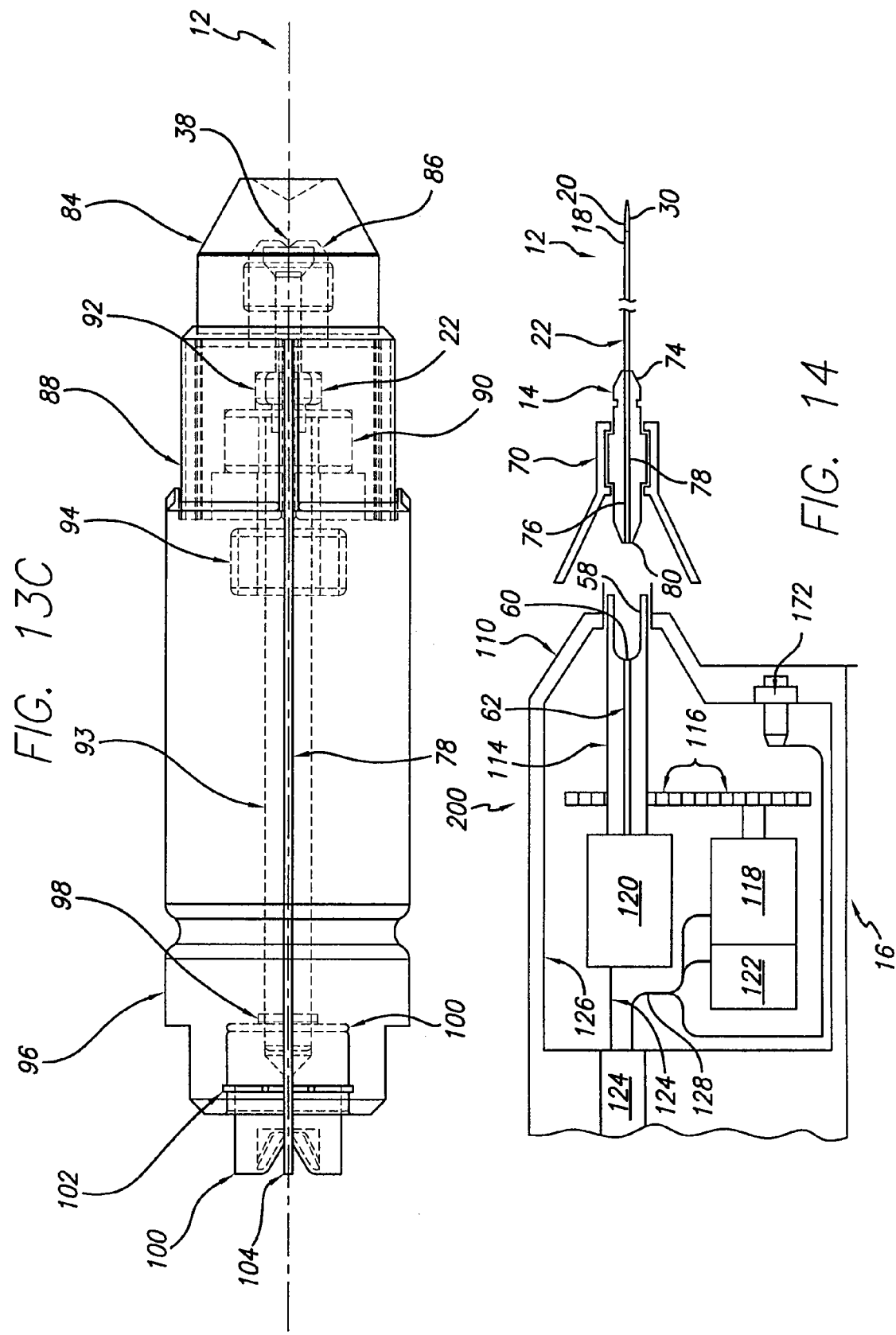

ROTATABLE FERRULES AND INTERFACES FOR USE WITH AN OPTICAL GUIDEWIRE

FIELD OF THE INVENTION

The invention is directed to intracorporeal optical devices for use within a body lumen, and devices and methods for connecting intracorporeal optical instruments with peripheral optical instruments. In particular, the invention is directed to a rotatable ferrule for use in an optical guidewire, interface devices for connecting an optical guidewire with peripheral devices, and methods for using these devices.

BACKGROUND OF THE INVENTION

Optical radiation can be used to view and to characterize tissues within a patient's body. Visible light may be useful, for example, for imaging and for acquiring spectroscopic information about a body lumen. Non-visible wavelengths may be useful as well. For example, intracorporeal devices sensitive to infrared radiation may be used to provide temperature information in order to identify diseased portions of a vessel wall. Such imaging devices typically use an optical fiber to carry light of visible and non-visible wavelengths.

Optical fibers convey optical radiation, and may be used to carry optical radiation from a source to a sensor. Optical fibers, particularly single-mode optical fibers, may be of extremely small diameters, as small as a few thousandths of an inch, making them suitable for introduction into small body lumens. Conveyance of optical radiation into and out of a body lumen is useful for imaging, spectroscopy, illumination, optical sensing, temperature sensing, photoactivation of drugs and compounds at an intraluminal location, photoablation, optical heating, and other applications. Optical instruments may use light of visible or of non-visible wavelengths. Visible light may be useful, for example, for imaging and for acquiring spectroscopic information about a body lumen.

For example, intracorporeal imaging is useful for diagnosing and treating many serious medical conditions such as, for example, arteriosclerosis. Intracorporeal optical imaging devices have been described, as in Brezinski et al., *Circulation* 93:1206-1213 (1996); Tearney et al., *Optics Letters* 21:543-545 (1996); Tearney et al., *Science* 276:2037-2039 (1997); Brezinski et al., *J. Surgical Research* 71:32-40 (1997); Brezinski et al., *Heart* 77:397-403 (1996); and Fujimoto et al., *Annals N.Y. Acad. Sci.* 838:95-107 (1998). Intracorporeal optical imaging devices have been described, as in U.S. Pat. Nos. 5,321,501 and 5,459,570 to Swanson et al., and U.S. Pat. No. 6,134,003 to Tearney et al. Non-visible wavelengths may be useful as well. For example, optical catheters sensitive to infrared radiation may be used to provide temperature information in order to identify diseased portions of a vessel wall, as disclosed in U.S. Pat. No. 5,935,075 to Cassells et al. All patents and patent applications, both supra and infra, are hereby incorporated by reference in their entirety.

Introduction and advancement of intracorporeal instruments through body lumens is typically aided by a guidewire, which is a thin, flexible device used to provide a guiding rail to a desired location within the vasculature (or other body cavity) of a patient. Following positioning of the guidewire, other larger or more fragile instruments may be guided to the desired location along the guidewire.

In angioplasty and other intraluminal procedures, guidewires are used to carry or guide devices such as catheters to their desired locations. It is preferred that guidewires be capable of loading and unloading different catheters or other devices, as different devices are often required or desired during a single clinical procedure. A guidewire that is used to carry, load or unload other intracorporeal instruments or devices is termed to be used in its therapeutic mode. Most guidewires are capable of being used only in therapeutic mode.

In addition to guiding and carrying other devices, guidewires may themselves be clinical instruments, as, e.g., when the guidewire is an optical guidewire (OGW) such as an optical imaging guidewire capable of receiving and transmitting optical radiation from within the body lumen for obtaining an image or an optical guidewire adapted to measure temperature or other physical characteristic within a body lumen.

A guidewire that is used as an optical instrument is used in "optical mode." Reception of optical radiation from within a body lumen provides clinicians with information useful in many clinical situations and procedures. Intracorporeal optical imaging is useful for the placement of guidewires, catheters, endoscopes, and other instruments in desired locations within a patient's body, such as within a blood vessel during angioplasty or the colon during colonoscopy. Optical imaging or spectroscopy of an artery and artery wall can provide information about the type, severity and extent of an occlusion or lesion and so improve the diagnosis and treatment of the patient. Optical radiation may be used to heat or ablate tissue, or to activate or inhibit photosensitive compounds located within a body lumen. Thus receiving and emitting optical radiation by an intracorporeal instrument can be of great importance to the success of a clinical procedure.

Reception of or emission of optical radiation directed to more than a single particular region within body lumen often requires rotation and longitudinal translation of the imaging guidewire in order to obtain images from a variety of orientations and positions within a body lumen. In order to obtain, display or analyze optical radiation, a guidewire must often be connected with external equipment such as a light source and image acquisition instrumentation. In addition, optical instruments may be rotated to provide a full view of regions of interest. Thus, a secure mechanical connection is required in order to accurately and stably control the location of a guidewire in guiding mode and to insure that images are faithfully transmitted when an OGW is used in optical mode. Moreover, it is imperative that the sterility of the guidewire be maintained during clinical procedures. In addition, it is preferred that clinical procedures be as rapid and efficient as possible. It is often useful to capture an optical fiber with a rigid or durable sleeve to protect the fiber and to provide an effective mechanical connection between an optical fiber and other devices. Such a sleeve is termed a "ferrule."

Accordingly, devices and methods for rotating an OGW and for effecting optical connections between an OGW and other equipment, including devices and methods for easily, securely and sterilely connecting and disconnecting an optical guidewire to non-sterile equipment are desired.

SUMMARY OF THE INVENTION

The invention is directed to intracorporeal optical instruments and methods for using intracorporeal optical instruments. Such instruments and methods may be used to direct optical radiation into an internal body lumen, and to direct optical radiation out of a body lumen, effective, for example, to illuminate a lumen, to obtain an image from within a lumen, or to provide a rotational scan of internal body lumens. In particular, the invention is directed to intracorporeal optical instruments such as optical guidewires (OGWs) having rotatable ferrules attached to optical assemblies, and related devices, systems and methods. OGWs may be used in therapeutic mode as guiding rails to guide other instruments (such as, e.g., catheters) to a desired location within a patient's body, or in optical mode to receive or emit optical radiation within a patient's body. OGWs embodying features of the invention have an elongated shaft, or hollow guidewire body (termed a hypotube) with an optical pathway and enclosing an optical assembly, and a ferrule engaged with or connected to the proximal end of the hypotube.

The hypotube has a bore extending at least part way therethrough that is configured to house at least part of the optical assembly. An optical assembly attached to a ferrule is disposed at least in part within the bore. An optical pathway may be a window or an aperture, or any feature suitable for passing optical radiation. An optical assembly includes an optical fiber, and such optical components as a lens, a mirror, or a prism. The optical fiber is typically a single-mode optical fiber. The optical assembly is attached to the ferrule, and may be used to carry light received at the distal end of the optical assembly in a proximal direction, and to carry light distally to be emitted from the distal end of the optical assembly. When the ferrule is rotated, the optical assembly rotates as well. Rotation of the ferrule and optical assembly rotates the direction of emission of light from the OGW, and rotates the direction from which light may be received by the optical assembly as well.

The ferrule has a distal portion that is configured to fit inside the proximal end of the hypotube; in such a case, the diameter of the ferrule distal portion may be the same, or less than the diameter of the proximal portion of the ferrule. The ferrule distal portion that is configured to engage an internal surface of the hypotube may be a surface selected from the group consisting of cylindrical surfaces, tapered surfaces, rounded surfaces, and combinations thereof.

In some embodiments of the invention, the ferrule is configured to have a releasable engagement whereby it is secured to the hypotube in a first position, and is released from the hypotube and free to rotate in a second position. For example, a releasable engagement is formed where a distal portion of the ferrule is pressed into a proximal portion of the hypotube to form a friction fitting between the ferrule and the hypotube. Such a friction fitting is a releasable engagement, so that, when retracted from the hypotube, the ferrule may rotate around a longitudinal axis without rotating the hypotube. Thus, the ferrule is securely engaged with the hypotube for use in therapeutic mode, while in optical mode the ferrule is retracted and released from the bore of the hypotube.

In other embodiments of the invention, a ferrule is rotatably engaged with a hypotube, where the ferrule is longitudinally constrained relative to the hypotube while remaining free to rotate. In such embodiments, at least a portion of a rotatable ferrule is captured within a proximal portion of a hypotube and is able to rotate around a longitudinal axis without rotating the hypotube. For example, the ferrule may be constrained by a ridge on the internal surface of the proximal portion of the hypotube that is fitted into a circumferential slot or channel on the ferrule.

The distal portions of the ferrules of the invention are configured to engage a hypotube in together forming part of an OGW embodying features of the invention. In addition, ferrules embodying features of the invention may have proximal portions configured to engage an interface or an external instrument. An interface may be, for example, a sterile interface configured to engage a ferrule and to convey optical radiation and mechanical force to and from the ferrule. An external instrument may be, for example, an optical instrument, a mechanical instrument, or both an optical and mechanical instrument. Thus, an OGW embodying features of the invention may form part of a system including an OGW and an interface; an OGW and an external instrument; and an OGW, an interface, and an external instrument.

Thus, as part of an OGW, the ferrules of the invention engage a hypotube effective to be able to rotate in the absence of hypotube rotation. Ferrules may also be configured to engage other optical and/or mechanical instruments. For example, optical instruments including optical fibers, amplifiers, digital and analog cameras, and so forth, may be connected with ferrules effective to transfer optical radiation from an OGW to other instruments for analyzing, recording, or otherwise processing optical radiation. Mechanical instruments, such as a motor for a rotating ferrule, must also be connected. Thus, the ferrules of the invention may further be configured for the formation of an operable optical connection with another optical instrument, and may be configured for the formation of an operable mechanical connection with another instrument. For example, the proximal portion of the ferrule may have an outer surface selected from the group consisting of cylindrical surfaces, tapered surfaces, rounded surfaces, and combinations thereof.

The invention further provides systems including an intracorporeal optical guidewire and an optical instrument having an optical connector and a rotatable mechanical connector. The optical guidewires of the systems include an elongated shaft having an optical pathway configured for passing optical radiation, and an internal chamber within the elongated shaft extending to the optical pathway, an elongated optical fiber disposed within the elongated shaft; and a ferrule attached to the optical fiber and configured to have a position in which the ferrule is free to rotate. The ferrules of the system are configured to engage the optical and the rotatable mechanical connectors. Rotation of the mechanical connector rotates the ferrule while the ferrule is engaged to the mechanical connector. In embodiments of the invention, the ferrule may rotate while at least part of the ferrule is disposed within the elongated shaft; in other embodiments, the ferrule is free to rotate when disengaged from and external to the elongated shaft.

During use in clinical procedures, the OGWs and optical and mechanical instruments must be connected so as to maintain the sterility of the OGW. Accordingly, devices embodying features of the invention may further include a sterile interface between an OGW and peripheral instrumentation. Such sterile interface devices are termed "sterile quick disconnection" (SQD) devices to denote their utility in enabling the rapid and convenient connection and disconnection with non-sterile equipment connected to the OGWs, such as peripheral imaging instrumentation, mechanical positioning instruments, and other peripheral equipment.

A SQD serves as an interface between an OGW and non-sterile external optical instrumentation. The non-sterile optical instrumentation may itself be an interface or may comprise a light source, an image acquisition instrument, an image analysis instrument, or any other imaging instrument or device used during a clinical imaging procedure. A SQD allows the proximal end of an OGW to be repeatedly connected and disconnected from non-sterile instruments while maintaining the sterility of the OGW. A SQD provides for disconnection of an OGW from external equipment, enabling catheters to be loaded and unloaded from the proximal end of an OGW during clinical procedures for use in therapeutic mode. In this way, the OGW is able to serve in its therapeutic mode to guide other intracorporeal instruments and to perform its imaging function in its optical mode.

An embodiment of a SQD includes a receptacle for engaging a ferrule, an optical fiber effective to carry optical radiation, a portion configured to engage a peripheral instrument, and optionally a sterile shield. The receptacle for engaging a ferrule may, for example, form a friction fit with the ferrule effective to secure the ferrule to the SQD.

In further embodiments, devices embodying features of the invention provide an external optical instrument providing optical interface with an SQD and having at least one of a source of optical radiation, an optical sensor, and a source of rotary power. In embodiments of the invention, such an external optical instrument (termed a Physician Interface Unit, or PIU) is configured for use by a clinician during a clinical procedure and may be sized so as to allow it to be manually held by an operator during use.

The invention further provides methods for using OGWs having rotatable ferrules. In embodiments of the method where the ferrule is configured to rotate freely within the internal chamber, the invention further provides a method for rotating an optical fiber disposed within an elongated shaft, including a) engaging a ferrule attached to an optical fiber disposed within an elongated shaft with an optical interface, b) engaging the ferrule with a mechanical interface with the ferrule, and c), rotating the mechanical interface effective to rotate the ferrule and the optical fiber. In embodiments of the invention where the ferrule is configured to form a friction fit within said internal chamber, the method further includes retracting the ferrule before rotating the ferrule effective to disengage the ferrule from a friction fit within the elongated shaft.

Ferrules of the invention provide the advantage of imparting rotation to an internal optical fiber without imparting rotation to the guidewire body. This advantage avoids possible damage to body tissue surrounding an OGW that might be caused by rotation of the guidewire, and avoids the need for a sheath around an imaging guidewire to protect against such tissue damage. In addition, ferrules of the invention provide the advantages of secure engagement with the hypotube while providing support for optical fibers and enabling effective optical connection with other optical devices. The ferrules provide effective use of the OGW in therapeutic mode, provide effective optical connections for use in optical mode, and are effective to provide rotational motion for rotational scanning with OGW optical elements in optical mode. The ferrules of the invention are thus effective to provide OGWs capable of dual use in both therapeutic and optical mode.

A SQD provides the advantages of maintaining the sterility of an OGW during a clinical procedure while the OGW is operatively engaged with peripheral optical instrumentation, while still allowing for disconnection of the OGW from peripheral optical instruments to allow the simple and easy interchange of catheters and other intracorporeal instruments carried by the guidewire. Thus, the SQD enables the dual use of an OGW in imaging mode as an imaging instrument without compromising its sterility for use in its guiding mode as a guidewire to guide the placement of other intracorporeal instruments in a body lumen.

The PIU provides the advantages of ease of use, portability, and maneuverability while providing the optical radiation and optical sensing function required for OGW use.

BRIEF DESCRIPTION OF THE DRAWINGS

FIG. 3A is a longitudinal cross-sectional view of an OGW comprising a rotatable ferrule embodying features of the invention releasably engaged with the proximal end of the hypotube of the guidewire.

FIG. 3B is a transverse cross-sectional view of the OGW of FIG. 3A taken along line 3B-3B.

FIG. 3C is a transverse cross-sectional view of the OGW of FIG. 3A taken along line 3C-3C.

FIG. 3D is a transverse cross-sectional view of the OGW of FIG. 3A taken along line 3D-3D.

FIG. 4A is a longitudinal cross-sectional view of an OGW comprising a rotatable ferrule embodying features of the invention rotatably engaged with the proximal end of the hypotube of the guidewire.

FIG. 4B is a transverse cross-sectional view of the OGW of FIG. 4A taken along line 4B-4B.

FIG. 4C is a transverse cross-sectional view of the OGW of FIG. 4A taken along line 4C-4C.

FIG. 4D is a transverse cross-sectional view of the OGW of FIG. 4A taken along line 4D-4D.

FIG. 4E is a transverse cross-sectional view of the OGW of FIG. 4A taken along line 4E-4E.

FIG. 5A is a perspective view of a rotatable ferrule and attached optical assembly embodying features of the invention having a distal portion configured to engage an OGW.

FIG. 5B is a longitudinal cross-sectional view of the ferrule and optical assembly of FIG. 5A.

FIG. 5C is a transverse cross-sectional view of the ferrule of FIG. 5A taken along line 5C-5C.

FIG. 5D is a transverse cross-sectional view of the ferrule of FIG. 5A taken along line 5D-5D.

FIG. 6A is a perspective view of a rotatable ferrule and attached optical assembly embodying features of the invention having a tapered distal portion configured to engage an OGW.

FIG. 6B is a longitudinal cross-sectional view of the ferrule and optical assembly of FIG. 6A.

FIG. 6C is a transverse cross-sectional view of the ferrule of FIG. 6A taken along line 6C-6C.

FIG. 6D is a transverse cross-sectional view of the ferrule of FIG. 6A taken along line 6D-6D.

FIG. 7A is a perspective view of a rotatable ferrule and attached optical assembly embodying features of the invention having a rounded distal portion configured to engage an OGW.

FIG. 7B is a longitudinal cross-sectional view of the ferrule and optical assembly of FIG. 7A.

FIG. 7C is a transverse cross-sectional view of the ferrule of FIG. 7A taken along line 7C-7C.

FIG. 7D is a transverse cross-sectional view of the ferrule of FIG. 7A taken along line 7D-7D.

FIG. 8A is a perspective view of a rotatable ferrule and attached optical assembly embodying features of the invention having a conical distal portion configured to engage an OGW in a luer lock-type engagement.

FIG. 8B is a longitudinal cross-sectional view of the ferrule and optical assembly of FIG. 8A.

FIG. 8C is a transverse cross-sectional view of the ferrule of FIG. 8A taken along line 8C-8C.

FIG. 8D is a transverse cross-sectional view of the ferrule of FIG. 8A taken along line 8D-8D.

FIG. 9A is a perspective view of a rotatable ferrule and attached optical assembly embodying features of the invention, having a channel configured to engage a hypotube and to rotate within the proximal end of the hypotube.

FIG. 9B is a longitudinal cross-sectional view of a the rotatable ferrule and optical assembly of FIG. 9A.

FIG. 9C is a transverse cross-sectional view of the ferrule of FIG. 9A taken along line 9C-9C.

FIG. 9D is a transverse cross-sectional view of the ferrule of FIG. 9A taken along line 9D-9D.

FIG. 9E is a transverse cross-sectional view of the ferrule of FIG. 9A taken along line 9E-9E.

FIG. 10A is a perspective view of a rotatable ferrule and attached optical assembly embodying features of the invention, having a channel and tapered distal end and configured to rotate within the proximal end of the hypotube.

FIG. 10B is a longitudinal cross-sectional view of a the rotatable ferrule and optical assembly of FIG. 10A.

FIG. 10C is a transverse cross-sectional view of the ferrule of FIG. 10A taken along line 10C-10C.

FIG. 10D is a transverse cross-sectional view of the ferrule of FIG. 10A taken along line 10D-10D.

FIG. 10E is a transverse cross-sectional view of the ferrule of FIG. 10A taken along line 10E-10E.

FIG. 13A is a perspective view of a sterile quick-disconnect interface embodying features of the invention.

FIG. 13B is an exploded view of the sterile quick disconnect interface of FIG. 13A.

FIG. 13C is a cross-sectional view of the assembled sterile quick disconnect interface of FIG. 13A.

FIG. 14 is cross-sectional schematic view of a system including an optical guidewire with rotatable ferrule, a sterile quick disconnect interface, and a physician's interface unit embodying features of the invention.

DETAILED DESCRIPTION OF THE INVENTION

Figure 1:
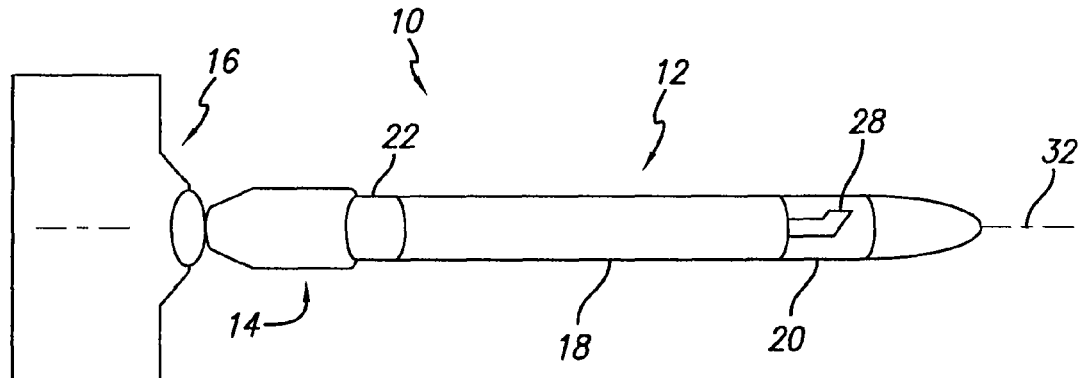
FIG. 1 illustrates a system embodying features of the invention having an optical guidewire (OGW) with a rotatable ferrule and a window and a sterile interface between the ferrule and an external optical instrument.

The system 10 of FIG. 1 includes an optical guidewire (OGW) 12 and a sterile quick disconnect interface (SQD) 14. The system 10 is shown in position to connect with an external optical and/or mechanical instrument 16 such as a Physician Interface Unit (PIU). The OGW has a hollow guidewire body 18, an optical pathway, and a ferrule 22. The hollow guidewire body (termed a "hypotube" 18) includes an elongate shaft with a bore. The optical pathway in this embodiment of the OGW 12 is a window 20 that provides an optical pathway into the hypotube 18. In other embodiments, the optical pathway includes an aperture or apertures 30. In some embodiments, the optical pathway may be in the tip of the elongate shaft. The ferrule 22 is rotatable. Enclosed within hypotube 18 and attached to the ferrule 22 is an optical assembly 24, which includes an optical fiber or fibers 26, and a directional assembly 28. The directional assembly 28 and a portion of optical fiber 26 is visible in FIG. 1 through window 20. OGW 12 is configured to receive, emit and convey optical radiation.

Optical radiation may be useful in imaging and optical sensing. The term "optical radiation" as used herein means electromagnetic radiation including but not limited to visible light, infrared radiation, ultraviolet radiation, and other radiation. Optical radiation may include radiation having wavelengths in the range between about 0.1 to about 3 micron, and may particularly include radiation having wavelengths in the range of between about 0.75 to about 2.5 micron or radiation having wavelengths in the range of between about 0.1 to about 1 micron.

Hypotubes, apertures and windows suitable for use in an OGW embodying features of the invention are disclosed in co-pending, co-owned application entitled "Optical Guidewires Having Windows or Apertures," to Jalisi et al., filed concurrently herewith, Ser. No. 10/024,986, hereby incorporated by reference in its entirety. Methods for forming windows suitable for use in an OGW embodying features of the invention are disclosed in co-pending, co-owned application entitled "Methods for Forming an Optical Window for an Intracorporeal Device and for Joining Parts," to Webler et al., Ser. No. 10/025,334, filed concurrently herewith, which is hereby incorporated by reference in its entirety.

Many of the terms which describe the elements of the systems and devices disclosed in the present application being now introduced, some definitions of particular terms follow.

The term "hollow" as used herein refers to an object at least a portion of which contains a cavity or space. Thus herein, a hollow guidewire is a guidewire with a bore at least partially therethrough. A hollow guidewire may have a solid end or ends, or other solid portion, as well as a portion containing a cavity.

The term "hypotube" as used herein means a hollow tubular object, in particular a hollow guidewire body. A hollow portion of a guidewire having a bore at least partially therethrough may thus be termed a hypotube. In particular, a hypotube may be at least part of the elongated shaft of an intracorporeal optical instrument. A hypotube has a wall, also termed a hypotube wall, or guidewire wall, which defines a bore within the hypotube.

The term "aperture" as used herein means a gap, hole or space in a material providing a communicating pathway from one side of the object to an other side of the object, such as in inside and an outside. The inside portion of the object may include a cavity within the object, or a bore therethrough, or may communicate with an internal solid portion of the object. An aperture may be regularly shaped, or irregularly shaped, of any size, and may be a gap in the wall of an object, such as a gap in a hypotube wall, or may be an opening into an end of an elongated hollow object.

The term "slot" as used herein means an elongated aperture having a length and a width, wherein the length is greater than the width. A slot may be straight, or curved or irregularly shaped, and may be of any size. A slot that extends to an end portion of a tube or shaft is termed "continuous" with the end of the tube or shaft. A slot that is continuous with the end of a tube or shaft facilitates the expansion of that end portion when that end is subjected to outward pressure, and is particularly effective to provide for a friction fit between a tube and an object that has been inserted into the bore of the tube adjacent the slot.

An "engagement" means holding, securing, or securely contacting, whether temporarily or permanently. Thus two objects are engaged when they are either temporarily or permanently secured to one another. A "releasable engagement" is a temporary engagement that may be released under the proper conditions. A "rotatable engagement" is an engagement that allows rotation of one or both the objects that are engaged while at the same time maintaining the engagement.

A "friction fit engagement" between two parts (also known as a pressure fit, press fit, or other such term) is one in which one part is forced into a receptacle or bore in another part and retained therein by the pressure exerted by the walls of the receptacle or bore. A friction fit may be temporary (i.e., releasable) or permanent. A releasable friction fit engagement is effective to secure and hold ferrule 12 and hypotube 14 together in the face of stresses that are expected to be encountered during the normal use of the OGW while being able to be released when desired by the operator.

The term "optical radiation" as used herein means electromagnetic radiation including but not limited to visible light, infrared radiation, ultraviolet radiation, and other radiation. Optical radiation may be useful in imaging and optical sensing. Optical radiation includes radiation having wavelengths in the range between about 0.1 to about 3 micron, and may particularly include radiation having wavelengths between about 0.75 to about 2.5 micron or radiation having wavelengths between about 0.1 to about 1 micron.

A "translucent material" is one that allows the passage of optical radiation through the material. A translucent material may transmit optical radiation without transmitting an image, although it may allow passage of optical radiation with so little distortion and diminution in intensity that it may transmit an image.

A "transparent material" allows optical radiation to pass through it so that an image may be observed through the material with little distortion or diminution in optical intensity. A transparent material thus allows transmission of optical radiation and of an image.

An "aperture" is an opening, gap, hole, or passage through a structure, such as a wall. Thus, for example, an opening in the wall of a hypotube that provides free passage of material from within the hypotube to regions outside a hypotube is an aperture.

A "window" is an element that allows the passage of optical radiation, whether visible or of other wavelengths, through a structure, such as a wall. An aperture that has been filled or blocked with a translucent or transparent material comprises a window.

A window or aperture may have the shape of a cylinder or of a portion of a cylinder. The outline or border of a window or aperture in a shaft is not a planar shape, but may be the projection of a planar shape onto a cylinder. Where the window or aperture shape is substantially the same as the shape of a geometric shape projected onto a cylinder, the window or aperture is described by the name of the geometric shape. Thus, e.g., a window or an aperture with a border having a shape substantially the same as the shape of a circle projected onto a cylinder is termed a circular window or aperture. Windows and apertures may, for example, have shapes selected from the group consisting of round, oval, square, rectangle, hexagon, octagon, other polygon, and irregular.

An "optical pathway" may be a window, aperture, plurality of windows or apertures, an optical fiber, a void, or any other object or material through which optical radiation is able to travel. An optical pathway provides a route for optical radiation to pass, to be carried or to be transmitted from one location to another, and so provides optical access between such locations. Optical communication includes passage of optical radiation between objects or between locations, where such radiation is present, or includes a pathway capable of effecting such passage of optical radiation in the event that optical radiation is not present. Typically, the components of an optical assembly, which may include an optical fiber and a lens or a prism, are in optical communication with each other. In addition, an operable optical connection between an optical fiber and a window or aperture means a connection effective so that at least some optical radiation passing through the window or aperture may enter or have been emitted from the optical fiber. There need not be physical contact between objects for there to be optical communication between the objects or locations.

An "optical fiber" is a thin elongated material effective to carry optical radiation from one location to another (e.g., from one end of the optical fiber to the other end). Optical fibers are typically made of glass which has been heated and stretched into very thin strands. Such glass fibers may be coated ("clad") so as to improve their optical performance and mechanical properties. Multiple strands of glass fibers may be loosely intertwined or bundled together, or may be packed and glued or clad together, to form fiber optic cables or optical assemblies. The term "optical fiber" is used herein to include a single optical fiber, a plurality of optical fibers, and an optical fiber assembly. Thus, an "optical fiber" may be a single strand (whether clad or not) or multiple strands of optical fibers, however clad, joined, glued or bundled together.

As used herein, a "ferrule" is a substantially cylindrical element attached to an end of an optical fiber. Ferrules typically aid in the mechanical manipulation of optical fibers by adding strength to optical fibers, making it possible to move and rotate the optical fibers with minimal risk of breakage.

In describing devices and methods embodying features of the invention, the OGW 12 of system 10 will be described first, and then the SQD 14 and PIU 16 will be described. Optical assembly 24 may include a single optical fiber, or a bundle of optical fibers. Optical fibers may be clad or wrapped with other materials for strength, reduction of friction, and/or to improve the efficiency of optical transmission. In some embodiments, an optical fiber may be a single-mode optical fiber. A ferrule 22 is attached to an end of the optical assembly 24, and may serve to strengthen and protect the optical fiber or fibers 26, and to facilitate the attachment of optical fiber or fibers 26 to other optical instruments.

Figure 2A:
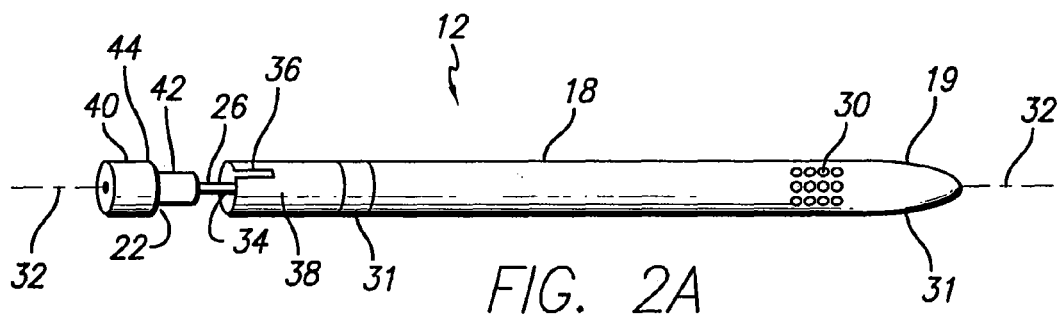
FIG. 2A is a perspective view of an OGW embodying features of the invention having a plurality of apertures and with a rotatable ferrule shown separated from the proximal end of the elongated shaft of the OGW.
Figure 2B:
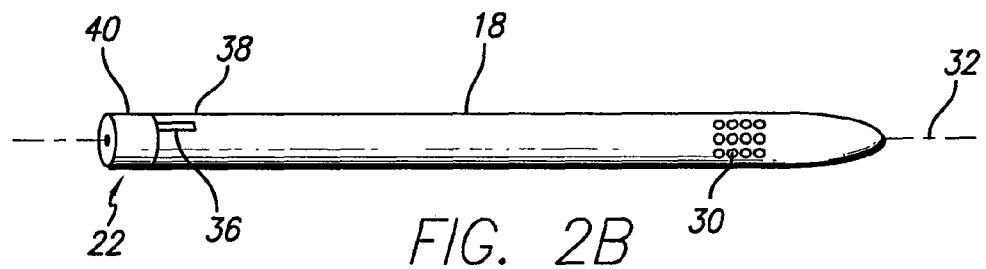
FIG. 2B is a perspective view of the OGW of FIG. 2A with the ferrule shown engaged with the elongated shaft of the OGW.
Figure 2C:
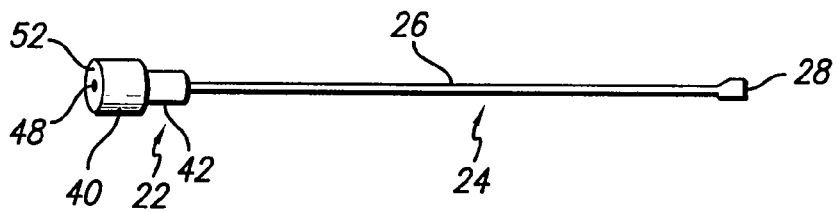
FIG. 2C illustrates the ferrule and attached optical assembly of the OGW of FIGS. 2A and 2B.

FIGS. 2A, 2B and 2C illustrate an OGW 12 having a ferrule 22 and hypotube 18 in which is housed an optical assembly 24 having an optical fiber 26 ending in a directional assembly 28 that may be a prism, lens (such as a graduated index of refraction lens, or GRIN lens) or other optical interface configured to direct optical radiation. In FIG. 2A, hypotube 18 has an optical pathway consisting of multiple apertures 30 suitable for passing optical radiation into and out of the hypotube 18, to and from directional assembly 28 of the optical assembly 24. Optical fiber 26 is suitable for carrying optical radiation. An optical fiber 26 may be effective, for example, to carry optical radiation so that optical radiation passing through a window 20 or aperture 30 and contacting directional assembly 28 connected to optical fiber 26 housed within hypotube 18 may be carried towards ferrule 22. In addition, optical radiation carried by optical assembly 24 may be emitted from directional assembly 28 at the end of optical assembly 24 and may pass out of a window 20 or an aperture 30.

The engagement between the hypotube 18 and the ferrule 22 of an OGW 12 embodying features of the invention is illustrated in FIG. 2. FIGS. 2A and 2B illustrate an OGW having a releasable engagement between hypotube 18 and ferrule 22, while FIG. 2D illustrates an OGW 12 having a rotatable engagement between hypotube 18 and ferrule 22. A releasable engagement is one in which a ferrule 22 may disengage and separate from a hypotube 18, while a rotatable engagement is one in which a ferrule 22 is free to rotate with respect to a hypotube 18 while engaged with hypotube 18. In a releasable engagement, a ferrule 22 is free to rotate with respect to a hypotube 18 when separated from the hypotube 18.

In FIG. 2A, an OGW 12 having a ferrule 22 configured for friction-fitting into a hypotube 18 is shown with the ferrule 22 released and retracted from the hypotube 18. The hypotube 18 is shown with radiopaque markings 31 at locations on a proximal hypotube portion 38 and a distal hypotube portion 19. Radiopaque markings 31 may comprise small markers, bands or other elements, or portions of a hypotube 18 that are radiopaque. The OGW 12 further has at least one slot 36 in the proximal portion 38 of the hypotube 18. The OGW 12 shown in FIGS. 2A and 2B also has a plurality of apertures 30 effective to pass optical radiation. A portion of optical fiber 26 is shown extending out from within bore 34 of hypotube 18 to indicate that the entire optical assembly 24 may fit within the hypotube 18 when a portion of ferrule 22 is inserted into hypotube 18. Optical fiber 26 is securely connected to ferrule 22. Movement of ferrule 22 along longitudinal axis 32 is effective to engage (via distal movement) or to disengage (via proximal movement) ferrule 22 from hypotube 18.

Ferrule 22 is shown having a circumferential step 44 at the juncture between proximal ferrule portion 40 and distal ferrule portion 42, the ferrule portions having different outer diameters. The outer diameter of distal ferrule portion 42 is configured to slip into and engage the bore 34 within proximal portion 38 of hypotube 18, the hypotube proximal portion 38 having an inner diameter large enough to accept ferrule distal portion 42. Slot 36 is configured to allow hypotube proximal portion 38 to expand effective to provide a releasable friction fit between distal ferrule portion 42 and proximal hypotube portion 38. Step 44 is effective to prevent insertion of the entire length of ferrule 22 inside bore 34 of hypotube 18.

When ferrule 22 is inserted into bore 34 and engaged in a friction fit with hypotube 18, the engagement between ferrule 22 and hypotube 18 is a secure engagement in which ferrule 22 cannot rotate with respect to hypotube 18. However, the friction fit is a releasable engagement between ferrule 22 and hypotube 18 so that ferrule 22 may retract from hypotube 18 and rotate with respect to hypotube 22 while retracted. A small amount of proximal translation of ferrule 22 along axis 32 away from hypotube 18, sufficient to remove ferrule distal portion 42 from within proximal portion 38 of hypotube 18, is effective to release the friction fit and to disengage ferrule 22 from hypotube 18. Since optical assembly 24 is attached to ferrule 22, optical assembly 24 and ferrule 22 may both rotate around longitudinal axis 32 without causing rotation of hypotube 22 when ferrule 22 is retracted from and disengaged from hypotube 18. The OGW 12 illustrated in FIG. 2A is thus configured in its optical mode.

Engagement of ferrule 22 by pressing ferrule distal portion 42 into proximal portion 38 of hypotube 18 securely connects ferrule 22 to hypotube 18 effective that OGW 12 may be used in therapeutic mode as a guidewire. The OGW 12 illustrated in FIG. 2B is thus configured in its therapeutic mode. Disengagement of ferrule 22 from proximal portion 38 of hypotube 18 by proximal movement of ferrule 22 generally along longitudinal axis 32 is effective to allow the free rotation of ferrule 22 and the attached optical assembly 24 without substantial interference from hypotube 18 and without substantially imparting rotational force or motion to hypotube 18. A hypotube suitable for forming a friction-fit engagement with a ferrule 22 may thus have a proximal portion 38 having a slot or slots 36, or a proximal portion 38 may be formed with expandable materials, or have an internal taper effective to form a friction-fit engagement similar to a luer-lock type friction fit.

FIG. 2C illustrates a ferrule 22 and optical assembly 24 configured for a releasable engagement with a hypotube 18 of an OGW 12. When in place within the bore 34 of a hypotube 18, directional assembly 28 is located adjacent an optical pathway through hypotube 18 (e.g., apertures 30 in FIG. 2A or window 20 in FIG. 1) effective that directional assembly 28 may receive or emit optical radiation through the optical path. During a clinical procedure where an OGW 12 is in place within a body lumen within a patient, such optical radiation emitted or received through the optical pathway would be emitted into or received from the body lumen.

Figure 2D:
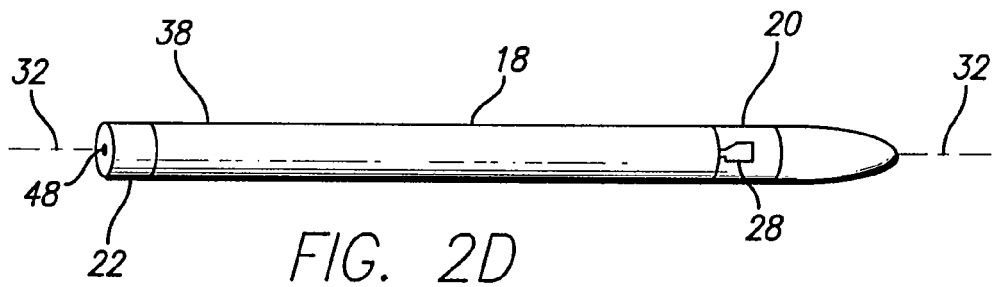
FIG. 2D illustrates an OGW embodying features of the invention with a ferrule rotatably captured and rotatably engaged with the elongated shaft of the OGW.
Figure 2E:
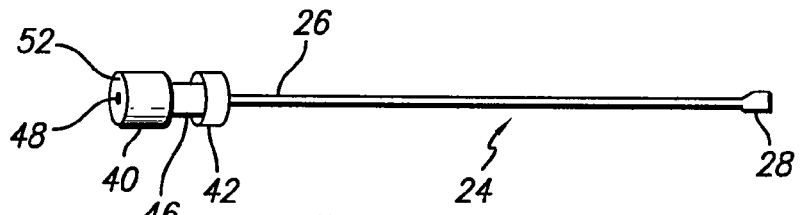
FIG. 2E illustrates a rotatable ferrule embodying features of the invention having a channel for engaging a hypotube, shown with attached optical fiber assembly.

In some embodiments of the invention, the engagement between ferrule 22 and hypotube 18 is a rotatable engagement rather than a releasable engagement. A rotatable engagement, as illustrated in FIGS. 2D and 2E, is one in which a ferrule 22 is free to rotate with respect to a hypotube 18 while engaged with hypotube 18. In other embodiments, as shown in FIGS. 2D and 2E, a ferrule 22 may be rotatably captured and rotatably engaged with a hypotube 18 of an OGW 12. In these embodiments, distal portion 42 of a ferrule 22 is housed within a bore 34 of a hypotube 18 and able to rotate therein without rotating hypotube 18. The distal portion 42 of a ferrule 2 may thus be rotatably captured, constrained and prevented from any substantial movement in a longitudinal direction but able to rotate around a longitudinal axis 32 without causing rotation of hypotube 18. FIG. 2E illustrates a rotatable ferrule 22 having a circumferential channel 46 separating proximal portion 40 from distal portion 42 and providing a means for hypotube 18 to capture ferrule 22 and to constrain its longitudinal motion without preventing rotational motion. Optical assembly 24, having optical fiber 26 and directional assembly 28 is shown attached to ferrule 22.

As illustrated in FIGS. 2D and 2E, optical fiber 26 of optical assembly 24 is held by and within ferrule 22 and extends from ferrule 22 within at least a portion of the length of hypotube 18, with a distal end configured with a directional assembly 28. Optical fiber 26 and directional assembly 28 are configured so that directional assembly 28 is located adjacent at least a portion of a window 20 (or an aperture 30) when ferrule 22 is engaged with and in place at least partly within hypotube 18 in the embodiment shown in FIG. 2D. Similarly, in an OGW having a releasable ferrule as illustrated in FIG. 2A the directional assembly 28 is located adjacent window 20 or aperture 30 when ferrule 22 is retracted and in a rotatable configuration. Optical radiation is able to pass through a window 20 or an aperture 30 to and from directional assembly 28 effective to be received or emitted by directional assembly 28. Optical radiation received or emitted by directional assembly 28 is conveyed along optical fiber 26 to and from proximal end 48 of optical fiber 26.

FIG. 3A is a longitudinal cross-sectional view of an OGW comprising a rotatable ferrule 22 embodying features of the invention releasably engaged with the proximal end of the hypotube of the guidewire. The hypotube 18 has at least one slot 36 in a proximal portion 38 of hypotube 18. As illustrated in FIG. 3A, distal portion 42 of ferrule 22 fits snugly inside proximal portion 38 of hypotube 18, the outer diameter of distal portion 42 being configured to form a releasable friction-fit engagement within proximal portion 38 of hypotube 18. In contact with ferrule distal portion 42, a proximal portion 38 of hypotube 18 extends around ferrule 22 up to circumferential step 44 of ferrule 22. In embodiments of the invention, the outer diameter of proximal portion 40 of ferrule 22 is configured to closely match the outer diameter of hypotube 18 effective to provide a substantially continuous external surface.

The ferrule 22 is illustrated as snugly fitted into proximal end 38 of hypotube 18. Proximal movement of ferrule 22 along axis 32 is effective to release the snug friction fit of ferrule 22 into proximal end 38 of hypotube 18 and to separate ferrule 22 from hypotube 18, as shown in FIG. 2A. Optical assembly 24, including optical fiber 26 and directional assembly 28, is securely attached to ferrule 22, and follows ferrule 22 when ferrule 22 is moved in any way. Rotation of ferrule 22 around axis 32 when disengaged from hypotube 18 does not substantially impart rotational motion of force to hypotube 18, and is effective to rotate optical fiber 26 and directional assembly 28 within hypotube 18 to provide rotational optical scanning motion for use in OGW optical imaging, sensing and radiation-emitting applications.

FIG. 3B is a transverse cross-sectional view of the OGW of FIG. 3A taken along line 3B-3B, showing optical fiber 26 within proximal portion 40 of ferrule 22. FIG. 3C is a transverse cross-sectional view taken along line 3C-3C, showing proximal portion 38 of hypotube 18 surrounding distal portion 42 of ferrule 22, and optical fiber 26 within ferrule 22. Optical fiber 26 is shown within bore 34 of hypotube 18 in the transverse cross-sectional view of the OGW shown in FIG. 3D.

FIG. 4A shows an OGW 12 with a rotatable ferrule 22 that is rotatably engaged with the proximal portion 38 of a hypotube 18. Proximal hypotube portion 38 has rim 50 configured to fit into and engage channel 46 which extends around the entire circumference of ferrule 22. Circumferential channel 46 is configured to slidably engage rim 50 of the proximal portion 38 of hypotube 18 allowing rotation of ferrule 22 within proximal portion 38 of hypotube 18. The slidable engagement between circumferential channel 46 and rim 50 is effective to prevent substantial longitudinal movement of ferrule 22 in either the distal or proximal direction, however, the slidable engagement between circumferential channel 46 and rim 50 allows free rotation of ferrule 22 around longitudinal axis 32 without substantial interference from hypotube 18, and without substantially imparting rotational force or motion to hypotube 18. Such rotation of ferrule 22 is effective to rotate optical fiber 26 and directional assembly 28 within hypotube 22 effective to provide rotational optical scanning motion to optical assembly 24.

Transverse cross-sectional views of the OGW 12 taken along lines 4B-4B, 4C-4C, 4D-4D and 4E-4E are shown in FIGS. 4B, 4C, 4D and 4E. Optical fiber 26 occupies a generally central position within ferrule 22 (FIGS. 4B, 4C and 4D) and hypotube 18 (FIG. 4E). The diameter of circumferential channel 46 shown in FIG. 4C is smaller than the diameter of ferrule portions 40 and 42 shown in FIGS. 4B and 4D.

FIG. 5A provides an illustration of a ferrule 22 embodying features of the invention, shown without hypotube 18 or other external components of OGW 12, although the attached optical assembly 24 (having optical fiber 26 and directional assembly 28) is shown, optical assembly 24 being an internal component of OGW 12. Ferrule 22 has a circumferential step 44 between a proximal ferrule portion 40 and a distal ferrule portion 42 having different outer diameters. The outer diameter of distal portion 42 is configured to fit within a proximal portion 38 of a hypotube 18 effective to provide a releasable friction-fit engagement between hypotube 18 and ferrule 20. The optical fiber 26 attached to the ferrule 22 and directional assembly 28 at the distal end of the optical fiber 26 are also shown in this figure. FIGS. 5B, 5C and 5D provide cross-sectional views of the ferrule illustrated in FIG. 5A. FIG. 5B is a longitudinal cross-section, and FIGS. 5C and 5D are transverse cross-sectional views taken along line 5C-5C and along line 5D-5D respectively.

FIG. 6A is a perspective view of a rotatable ferrule 22 and attached optical assembly 24 embodying features of the invention having a tapered distal portion 42 configured to engage a hypotube. Tapered distal portion 42 is effective to provide a friction-fit engagement between a proximal hypotube portion 38 and a ferrule 22. The tapered distal portion 42 is effective to engage an expandable proximal hypotube portion 38 (e.g., as shown in FIG. 2A), which may have a slot or slots 36 or may be formed of an expandable material with or without slots 36. The taper of distal ferrule portion 42 further aids in the proper location of ferrule 22 within bore 34 of hypotube 18 by acting to guide and center ferrule 22 as it is inserted into bore 34. FIG. 6B is a longitudinal cross-sectional view of the ferrule 22 and optical assembly 24 illustrated in FIG. 6A, and FIGS. 6C and 6D are transverse cross-sectional views of the ferrule of FIG. 6A taken along lines 6C-6C and 6D-6D respectively.

The ferrule 22 shown in FIG. 7 has a rounded distal portion 42 configured to engage a hypotube 18 of an OGW 12. The rounded distal portion 42 is effective to engage a proximal hypotube portion 38, which may have a slot or slots 36 or may be formed of an expandable material with or without slots 36, and aids in the proper location of ferrule 22 when inserted within hypotube 18. Cross sectional views are provided in FIGS. 7B-7D (longitudinal in FIG. 7B; transverse in FIGS. 7C and 7D).

FIG. 8A shows a perspective view, and FIGS. 8B-8D cross-sectional views, of a rotatable ferrule and attached optical assembly 24 embodying features of the invention having a conical distal portion 42 configured to engage a proximal portion 38 of a hypotube 18 of an OGW 12 in a luer lock-type engagement.

FIG. 9A shows a perspective view, and FIGS. 9B-9E cross-sectional views, of a ferrule configured for placement and rotation within a bore 34 of a hypotube 18 of OGW 12 having features of the embodiment illustrated, for example, in FIGS. 2D and 2E. Optical assembly 24, including an optical fiber 26 and a directional assembly 28, is attached to the ferrule 22. As shown in FIGS. 9A, 9B and 9D, in this embodiment ferrule 22 has a circumferential channel 46 which is configured to receive a rim 50 of a hypotube 18. FIG. 9C is a view of the ferrule 22 showing the proximal ferrule portion 40 in cross-section. FIG. 9E is a view of the ferrule 22 showing the distal ferrule portion 42 in cross-section. As illustrated in these figures, the diameter of channel section 46 is smaller than the diameter of either proximal portion 40 or distal portion 42 of a ferrule 22. Distal ferrule portion 42, configured to fit into and to rotate within a bore 34 within the proximal portion 38 of a hypotube 18, may have an outer diameter smaller than that of proximal portion 40. In some embodiments of the invention, the outer diameter of distal ferrule portion 42 is configured to fit inside a bore 34, and the diameter of channel 46 is configured to receive a rim 50 of a hypotube 18 having a rim 50, while proximal ferrule portion 40 may have any outer diameter suitable for interaction with a SQD or external optical interface 16 such as a PIU. When engaged with a rim 50, channel 46 is effective to constrain longitudinal movement of ferrule 22 with respect to hypotube 18 while allowing rotational movement of the ferrule 22 and attached optical assembly 24.

The rotatable ferrule 22 shown in FIG. 10A to FIG. 10E is also configured to fit into and rotate within a bore 34 of a hypotube 18. FIG. 10A is a perspective view of a rotatable ferrule 22 and attached optical assembly 24 having a channel 46 and tapered distal portion 42. Channel 46, shown in cross-section in FIG. 10D, has a smaller diameter than the adjacent regions of proximal ferrule portion 40 and distal ferrule portion 42; channel 48 is configured to receive a rim 50 at the end of the proximal portion 38 of a hypotube 18. Tapered distal ferrule portion 42 of the embodiments shown in FIGS. 10A through 10E may be readily inserted into a bore 34 in the proximal portion 38 of a hypotube 18, for example, during manufacture, the taper aiding in insertion of the ferrule 22 while allowing the capture of a rim 50 within channel 46 effective to constrain longitudinal movement of ferrule 22 with respect to hypotube 18 while allowing rotational movement of ferrule 22 and attached optical assembly 24.

Figure 11A:
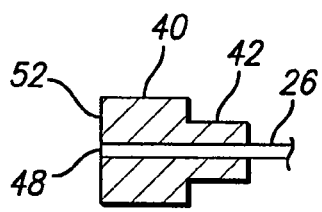
FIG. 11A is a longitudinal cross-sectional view of a ferrule embodying features of the invention having an optical fiber with proximal end flush with the proximal face of the ferrule.
Figure 11B:
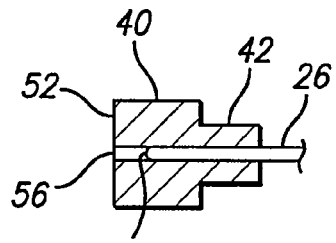
FIG. 11B is a longitudinal cross-sectional view of a ferrule embodying features of the invention having an optical fiber with proximal end recessed distally from the proximal face of the ferrule.
Figure 11C:
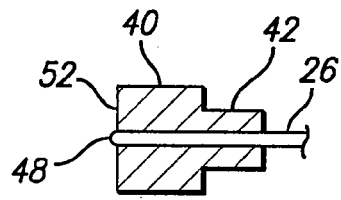
FIG. 11C is a longitudinal cross-sectional view of a ferrule embodying features of the invention having an optical fiber with proximal end extending in part proximally out of the proximal face of the ferrule.

In some instruments embodying features of the invention, optical fiber 26 of optical assembly 24 is enclosed by ferrule 22 within ferrule bore 56, and extends at least partially through ferrule 22 towards ferrule proximal face 52. In some embodiments, the proximal end 48 of optical fiber 26 extends to, and is flush with, ferrule proximal end 52, as illustrated in FIG. 11A. In some embodiments, optical fiber 26 does not extend completely through ferrule 24, and proximal end 48 of optical fiber 26 is located at a position within ferrule 22 distal to ferrule proximal face 52, as illustrated in FIG. 11B. In such embodiments where optical fiber proximal end 48 is recessed from ferrule proximal face 52, within ferrule bore 56, optical radiation is able to pass to and from optical fiber 24 through bore 56. In yet other embodiments, as illustrated in FIG. 11C, proximal end 48 of optical fiber 26 extends outwardly from ferrule proximal face 52. Optical fiber proximal end 48 may be configured so as to optimize transfer of optical radiation into and out of optical fiber 26. For example, in embodiments such as the one illustrated in FIG. 11A, optical fiber proximal end 48 may be polished to be smooth, flat, and perpendicular to longitudinal axis 32, forming a flat surface substantially continuous with ferrule interface 52. Alternatively, as in embodiments such as those illustrated in FIGS. 11B and 11C, the proximal end 48 of optical fiber 24 may be shaped, coated, or otherwise configured so as to promote effective optical coupling between optical radiation traversing optical fiber 24 and other optical devices. For example, proximal optical end 48 may be shaped to be concave, convex, or other shape so as to receive and emit optical radiation not only along a path parallel to longitudinal axis 32 but along other paths as well. In addition, proximal end 48 may be coated, or materials may be applied to optical fiber proximal end 48 to improve optical transmission and to improve mechanical contact between optical fiber 24 and other elements including other optical fibers, sources of optical radiation, and optical sensors. For example, materials such as oils may be applied to improve mechanical contacts and reduce friction during rotation, and to aid in matching of the indices of refraction of different optical elements that are configured to work together.

Thus, as shown in FIG. 11B, in embodiments of the invention a proximal end 48 of an optical fiber 26 may be located at a distance from ferrule proximal face 52 within a ferrule bore 56, effective that there is no physical contact between optical fiber 24 and an optical fiber in another element, such as a SQD 14, upon engagement of ferrule 22 with a SQD 14. Although sterility can be maintained when an optical fiber 24 is in contact with other instruments, a configuration as illustrated in FIG. 11B may be conducive to the maintenance of sterility of a fiber 22 and optical fiber 24 during clinical use of an OGW. Although the ferrules illustrated in FIGS. 11A-11C are similar to the ferrule illustrated in FIGS. 5A-5D, it will be understood that a ferrule 22 of any design, including designs illustrated in any of FIGS. 5-10, may have any of the configurations of optical fibers 24 and ferrules 22 shown in FIGS. 11A-11C.

Figure 12A:
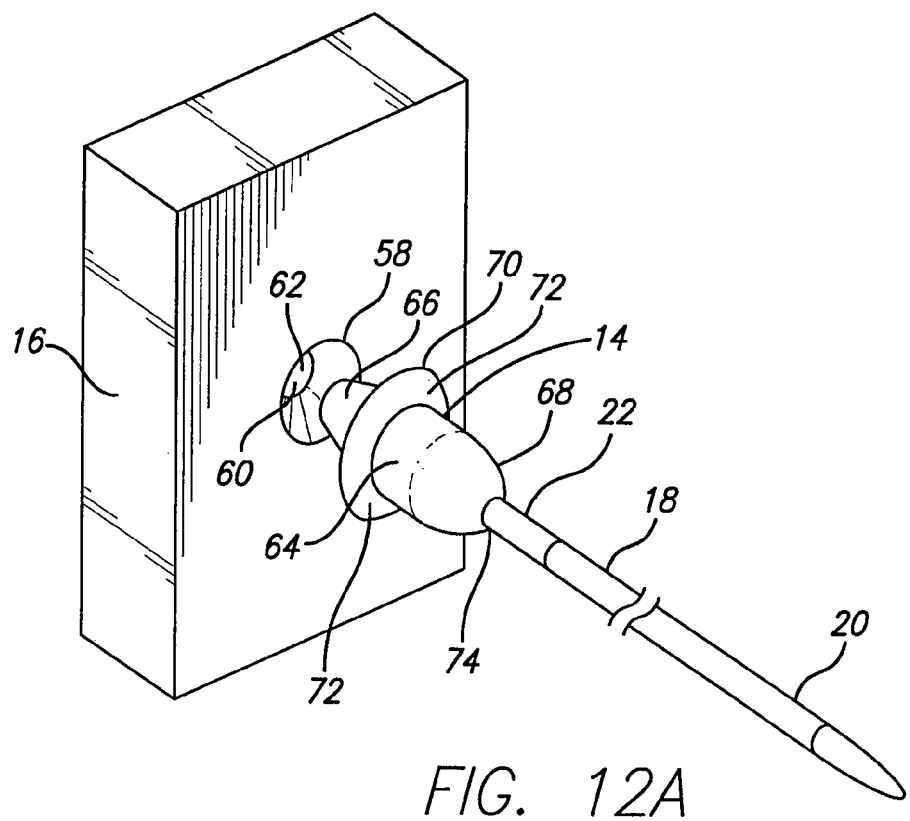
FIG. 12A illustrates a longitudinal cross-section of a system embodying features of the invention including an external optical and mechanical instrument, a sterile quick disconnect interface, and an OGW.

FIG. 12A is a perspective view of a system embodying features of the invention, including an external optical instrument 16, a SQD interface 14, and an OGW 12. The external optical instrument 16 has a docking port 58 and an optical port 60, which may include an optical fiber 62, which is configured for transmitting optical radiation into and out of the external optical instrument 16. In some embodiments, the external instrument 16 is both an optical and a mechanical instrument. For example, as a mechanical instrument, external instrument 16 may be effective to rotate an attached assembly of a SQD 14 and an OGW 12. As an optical instrument, external instrument 16 may be effective to emit and receive optical radiation via a SQD and an OGW. In some embodiments, external instrument 16 may be a portable instrument such as a physician's interface unit (PIU). The SQD 14 has a SQD body 64 having a proximal portion 66, a distal portion 68, and a receptacle 74 for receiving a ferrule 22 of an OGW 12. In some embodiments, the SQD has a shield 70 configured for maintaining the sterility of objects distal to it, at least in part by having a sterile distal surface 72 and by its presence and location providing a physical barrier between sterile and non-sterile regions. A shield 70 may be made of any suitable material capable of being sterilized and of presenting a physical barrier capable of maintaining the sterility of a region distal to the barrier. A shield 70 may include portions that are external to an SQD body 64, portions that are internal to an SQD body 64, or may be entirely external or internal to an SQD body 64.

Figure 12B:
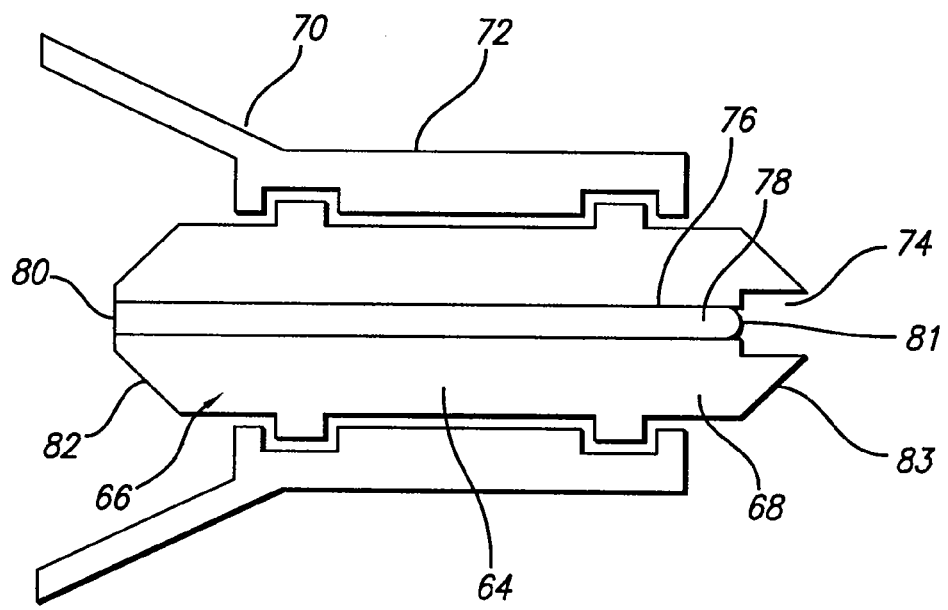
FIG. 12B illustrates a sterile quick-disconnect interface embodying features of the invention.

FIG. 12B illustrates an embodiment of an SQD interface 14 embodying features of the invention. The SQD 14 has a shield 70 with a sterile distal surface 72 configured to allow rotation of SQD body 64 while an OGW 12 rotates while secured to SQD 14 by receptacle 74. An optical channel 76 runs through SQD 14. Optical channel 76 may include an optical fiber 78 housed within optical channel 76. In some embodiments of the SQD, the optical fiber 78 comprises the entire optical channel 76. In some embodiments, the optical channel 76 may have an air gap or a gap filled by optically translucent or transparent material. SQD optical fiber 78 has a proximal end 80 and a distal end 81 which may be independently flat, perpendicular to the longitudinal axis 32 through optical channel 76, polished, curved, coated, or otherwise configured to optimize the transmission of optical radiation. The SQD has a proximal end 82 and a distal end 83. Optical fiber ends 80 and 81 may be independently located within optical channel 76, may extend out from SQD ends 82 and 83, or may be flush with SQD ends 82 and 83.

Receptacle 74 is configured to receive and hold a ferrule 22. For example, receptacle 74 may be configured with slots, channels, holes, ridges, or other designs, shaped with a taper, or formed partly or entirely of materials with a sufficient amount of elasticity so as to hold a ferrule 22 upon insertion of a ferrule 22 into receptacle 74 with a secure friction fit.

A SQD 14 having features of the invention is illustrated in FIGS. 13A-13C, and shown with an OGW 12 having features of the invention that is configured to contact an optical fiber 78 from the SQD. The SQD 14 is configured to immobilize the proximal hypotube 38 of an OGW 12 by rotating a collet lock 84 effective to close a collet 86 on the proximal hypotube 38 of an OGW 12 and a ferrule 22 may be separated from a hypotube 18 effective to firmly grip the OGW 12 in optical mode configuration.

In use of the SQD 14 illustrated in FIGS. 13A-13C, an optical fiber 78 is advanced so as to contact the optical fiber 26 of an OGW 12 or otherwise make an operable optical connection with the optical fiber 26 of an OGW 12. A ferrule 22 may be rotated while the SQD 14 makes contact or other form of operable optical connection with the optical fiber 26 of an OGW 12.

As shown in FIGS. 13A-13C, a SQD 14 may capture and engage an OGW 12 with a collet or collets. The embodiment of the SQD shown in FIGS. 13A, B, and C is configured to capture hypotube 18 and to capture ferrule 22 effective that ferrule 22 and optical assembly 24 are able to rotate while captured, and while hypotube 18 is held by SQD 14 and prevented from rotating. The SQD 14 illustrated in FIGS. 13A-13C is configured for use with an OGW 12 having a rotatable ferrule 22 releasably engaged with a hypotube 18, as illustrated in FIGS. 2A-2C; the SQD 14 is configured to capture hypotube 18 and ferule 22 and to separate ferrule 22 from hypotube 18. FIG. 13 A is a perspective view, FIG. 13B is an exploded view, and FIG. 13C is a cross-sectional view (assembled) of an SQD interface 14 configured to capture a hypotube 18 and a ferrule 22 and to separate the hypotube 18 from the ferrule 22.

Thus, in the embodiment shown in FIGS. 13A-13C, an OGW 12 of the embodiment shown in FIGS. 2A-2C is mated with a SQD 14 embodying features of the invention. The outer components of the SQD 14 illustrated in FIGS. 13A-13C include collet lock 84, distal housing 88, and proximal housing 96. The SQD 14 is configured with internal components, including a distal collet 86 and a proximal collet 92 which are effective to hold hypotube 18 and ferrule 22, and to separate the ferrule 22 of an OGW 12 from the proximal hypotube 38, putting the OGW 12 into imaging mode by readying it for rotation of the optical assembly 24.

The SQD 14 illustrated in FIGS. 13A, 13B and 13C is formed from an assembly of parts, with each part having a bore through it so that the bores together define a passage 76 through the SQD 14. The first step in configuring OGW 12 into imaging mode is to insert OGW 12 into receptacle 74 at the distal opening of passage 76 through SQD 14 so that ferrule 22 passes through distal collet 86 to contact proximal collet 92. Proximal collet 92 is configured to engage and hold ferrule 22. Distal collet 86 is configured to engage and hold the hypotube proximal portion 38 and to separate ferrule 22 from hypotube 18.

In the embodiment shown in FIG. 13A, distal housing 88 may be rotated into any of three positions with respect to proximal housing 96, termed position I, position II, and position III. These positions correspond to the positions taken by distal housing 88 and proximal housing 96 when notch 97 is lined up with groove 88A (position I), either of grooves 88B (position II), or any of grooves 88C (position III). These parts may be secured into a desired position by any suitable means, including locks, clips, clamps, slides, or other means. For example, as illustrated in FIG. 13A, notch 97 may be configured as a detent able to partly fit into and engage with grooves 88A, 88B, and 88C, effective to hold distal housing 88 and proximal housing 96 into a desired position.

Positions I, II, and III correspond to configurations of SQD 14 that allow fitting of an OGW 12 into the SQD (position I), securely engaging an OGW 12 with the SQD 14 (position II), and separating the ferrule 22 from the hypotube 18 of an OGW 12 while providing secure optical contact between the optical fiber 26 of an OGW 12 and the optical fiber 78 of an SQD 14. In position III, the secure optical contact is maintained while rotational motion is imparted to ferrule 22 and optical fiber 26 without rotating hypotube 18.

Referring to FIGS. 13B and 13C, it may be seen that the parts of the assembly include a distal collet lock 84 enclosing a distal collet 86, the distal collet 86 being held by a distal housing 88. A proximal collet lock 90 engages a proximal collet 92 fitted within bores through proximal collet lock 90 and housing connector 94. Housing connector 94 has male threads configured to mate with threads of the distal housing 88, effective that rotation of housing connector 94 moves housing connector 94 with respect to distal housing 88. It will be understood that any suitable method for effecting relative motion between distal housing 88 and housing connector 94 may be used in other embodiments of the invention. The proximal collet 92 has a long shaft 93 extending proximally within bores through proximal collet lock 90 and housing connector 94, the proximal collet 92 extending distally of the proximal collet lock 90 and extends proximally into proximal housing 96. Housing connector 94 is permanently secured (e.g., pressed or glued) into proximal housing 96.

An O-ring 98, which serves as an internal sterile barrier, similar to sterile shield 70 shown in FIG. 12B, slips around the shaft 93 of proximal collet 92, forming a seal and separating the proximal housing 96 from drive connector 100. Drive connector 100 serves to connect the rotating parts of SQD 14 to a mechanical rotary drive, such as may be part of an external optical and mechanical instrument 16. Drive connector 100 is held in place by snap ring 102. Fixed fiber guide 104 slides through bores in the assembled parts (the bores together forming an optical channel 76), surrounding and enclosing optical fiber 78, to support and protect optical fiber 78 in its position within proximal collet 92. The optical fiber 78 is configured and positioned so as to make operable optical contact with optical fiber 26 in ferrule 22 when the SQD 14 captures and holds an OGW 12.

Positioning SQD 14 into position I with distal housing 88 and proximal housing 96 aligned so that groove 88A substantially lines up with notch 97 is effective to place distal collet 86 and proximal collet 92 in their relatively open positions, allowing an OGW 12 to slide freely within passage 76. Positioning SQD 14 into position II, with distal housing 88 and proximal housing 96 aligned so that a groove 88B substantially lines up with notch 97 is effective to place distal collet 86 and proximal collet 92 into their relatively closed positions so that distal collet 88 and proximal collet 92 firmly grip an OGW 12 within the SQD 14. Positioning SQD 14 into position III, with distal housing 88 and proximal housing 96 aligned so that a groove 88C substantially lines up with notch 97 is effective to place distal collet 86 and proximal collet 92 into their relatively closed positions and to separate proximal collet 92 from distal collet 88 so that a ferrule 22 firmly gripped by proximal collet 92 is pulled away from a proximal hypotube 38 firmly gripped by distal collet 88 within the SQD 14.

SQD 14 as illustrated in FIGS. 13A-13C provides an operable optical connection between an OGW and the SQD effective that optical radiation transmitted by the OGW is effectively transmitted by the SQD to and from an operator or to and from an external optical instrument or source of optical radiation. In use, an OGW is inserted into the collet lock 84 to contact the end of the SQD optical fiber 78 making an operable optical connection. Such contact may include direct contact between optical fiber 26 and optical fiber 78, or contact between optical fiber 78 and proximal ferrule face 52, or optical fiber 78 may be inserted at least partially into ferrule bore 56 (e.g., as illustrated in FIG. 11B). The contact is secured by locking distal collet 86 onto a proximal portion 38 of hypotube 18, and locking proximal collet 92 onto ferrule 22. Contact between optical fibers 26 and 78 is accomplished by turning distal housing 88 from a first position to a second position. Immobilization of the OGW in imaging mode is accomplished by turning collet lock 84 clockwise, which in turn closes distal collet 86 onto proximal hypotube portion 38, and by turning distal housing 88 from a second position to a third position effective to pull ferrule 22 in a proximal direction, thereby releasing it from its releasable engagement with the proximal hypotube portion 38.

For example, by turning housing connector 94 and proximal housing 96 so that the threads engage those of distal housing 88, proximal collet 92 is pressed into proximal collet lock 90, closing proximal collet 92 around ferrule 20 (position II) and retracting ferrule 20 from proximal hypotube portion 38, releasing the ferrule 22 from its engagement with hypotube 18 (but not with SQD 14) and allowing it to rotate without rotating hypotube 18 (position III).

The SQD 14 is also effective to return ferrule 22 into a secure engagement with hypotube 18. Turning distal housing 88 from a third position to a second position pushes ferrule 22 into hypotube proximal portion 38 to form a friction fit between ferrule 22 and hypotube 18 (position II). Release of the OGW 12 is accomplished by next turning distal housing 88 from a second position to a first position, which in turn pushes the proximal collet 92 out of the proximal collet lock 90, opening the proximal collet 92 and releasing the OGW 12 (position I).

The distal motion of distal housing 88 releases distal collet lock 84 releasing distal collet 86 and releasing proximal hypotube 38, allowing its removal from the SQD 14. Complete release of the hypotube 18 is accomplished by turning the collet lock 84 counterclockwise opening distal collet 86. Upon release from SQD 14, with ferrule 22 engaged within hypotube 18, the OGW 12 is then configured for use in therapeutic mode.

In the embodiments illustrated in FIGS. 13A to 13C, sterile shield 70 is a seal, such as O-ring 98, which is sterile and effective to seal onto proximal collet 92 to form a physical separation between regions proximal and distal of the seal 70. A sterile shield 70 providing a sliding contact such as shown in this embodiment allows longitudinal motion of other components of the SQD while maintaining sterile separation between sterile region distal of the shield 70 and a non-sterile region proximal of the shield 70. Also shown in FIGS. 13A-13C is drive 98, configured to engage a mechanical rotary drive mechanism so as to provide rotational force to components of the SQD 14 and to the ferrule 22 and optical assembly 24 when the ferrule 22 and optical assembly 24 are engaged by SQD 14. Snap ring 100 is effective to hold drive 98 against proximal housing 96 to provide for effective transfer of rotational energy to the SQD 14. Rotational force may be supplied by, for example, an external optical and mechanical instrument 16 such as a physician's interface unit.

Where the optical guidewire captured and held by SQD 14 has a rotatable ferrule as illustrated in FIGS. 2D and 2E, no separation between ferrule 22 and hypotube 18 is effected. Thus, an SQD 14 for use with a rotatable ferrule as illustrated in FIGS. 2D and 2E does not require longitudinal movement and does not separate distal collet 86 and proximal collet 92. In use with an OGW embodying features illustrated in FIGS. 2D and 2E, an SQD 14 as illustrated in FIGS. 13A-13C needs only to engage a distal collet 86 onto proximal hypotube portion 38, and to engage a proximal collet 92 onto a ferrule 22, allowing rotation of proximal collet 92 and ferrule 22 while holding distal collet 86 and proximal hypotube portion 38 relatively fixed so as not to rotate distal collet 86 and proximal hypotube portion 38 while proximal collet 92 and ferrule 22 rotate.

FIG. 14 is cross-sectional schematic view of a system 200 embodying features of the invention, including an optical guidewire with rotatable ferrule 22, a SQD interface 14, as illustrated in FIG. 12B, and a PIU 16. Thus, the system 200 illustrated in FIG. 14 includes a PIU 16 and a system 10 as illustrated in FIG. 1. The PIU 16 illustrated in FIG. 14 includes an optical device having a mechanical connector 58 and an optical connector 60, an optical instrument (or instruments) 120 effective to produce and to detect optical radiation, and a rotary drive (e.g., gears 116 connected to motor 118) effective to rotate the mechanical connector 58 and the optical connector 60 and other objects connected to them. The system 200 includes an OGW 12 having a rotatable ferrule 22 embodying features of the invention. In particular, the system 200 illustrated in FIG. 14, having OGW 12, SQD 14 and PIU 16 is shown with components slightly separated one from the other, indicating the releasability of the connections between them. It will be understood that OGW 12, SQD 14 and PIU 16 may be joined to form operative optical connections between the respective component parts.

It will be understood that the engagement of ferrule 22 by mechanical connection 58 may be either direct or indirect. That is, ferrule 22 may directly engage mechanical interface 58 and/or optical interface 60, or, alternatively, an intermediate connector, connection device or connection assembly such as a SQD 14 may be employed between ferrule 22 and other connectors, or along with ferrule 22, effective to engage ferrule 22 with a mechanical interface 58 and/or optical interface 60. Rotation of ferrule 22 is effective to rotate optical assembly 24 within the hypotube 18.

As illustrated in FIG. 14, the outer surface of PIU 16 includes an enclosure 110 which may be configured as a sterile cover and/or a durable case. Other elements readily accessible to an operator of a PIU 16 embodying features of the invention may include controls such as an on/off switch 112. Internal elements of a PIU 16 embodying features of the invention may include a shaft or hollow axle 114 operably connected to gears 116 and to a motor 118 effective to impart rotational motion to docking portion 58 of the PIU 16. The rotation of docking port 58, when occupied by an SQD 14 engaged with an OGW 12, is effective to effect rotation of a ferrule 22 and attached optical assembly 24 of the OGW 12 effective to provide a rotational scan of regions adjacent a window 20 or aperture 30 of the OGW 12.

Optical radiation passing to and from optical assembly 24 of an OGW 12, and via an optical channel 76 of an SQD 14, may pass to and from optical port 60 via optical fiber 62 and optional coupling optics 120 (which may include electro-optical devices such as lenses, prisms, mirrors, video cameras, photomultipliers, charge-coupled devices, and other optical and electronic equipment) and electro-optical cable 124 from a source of optical radiation, and/or to detection, recording and analysis devices. Electrical signals may be carried by cables 128 or other electrical connections. An angle encoder 122 may be used to detect, control and record the angular position of an internal component. PIU internal components may be connected together and to enclosure 110 by connector parts 126.

In the system 200 illustrated in FIG. 14, a continuous optical pathway extends in a proximal direction from an OGW 12 (having, for example, as illustrated in FIGS. 2-4, a window 20 or aperture 30 in the distal portion of a hypotube 18, effective to transmit light to a directional assembly 28 along optical fiber 26 to the proximal end 48 of optical fiber 26), and into optical channel 76 of SQD 14, which may include an optical fiber 78, and then to the optical port 60 of external optical and mechanical instrument 16 where optical radiation may pass directly to an optical instrument 104 or may pass along an optical fiber 62 to or through coupling optics 120. Coupling optics 120 may also include a source of optical radiation for transfer of optical radiation in the opposite direction. Optical information, whether in optical form or transformed into electronic or electro-optical form, may be further passed along an electro-optical cable 124. Where the direction of optical radiation transfer is in a distal direction, optical radiation from an optical source at, e.g., 120, may pass along an optical fiber 62 to optical port 60, through optical channel 76 of SQD 14 to optical assembly 24 of OGW 12, passing along optical fiber 26 of optical assembly 24, and then from directional assembly 28 out of OGW 12 via window 20 and/or aperture 30. It will thus be understood that optical radiation may pass in both distal and proximal directions along part or all of the entire optical pathway just described.

It will be understood that in some embodiments of the invention, mechanical connection 58 and optical connection 60 may be combined together in a single device or assembly, such as a PIU 16, and in other embodiments mechanical connection 58 and optical connection 60 may be separate devices or assemblies.

Ferrules embodying features of the invention may be made from any suitable material, such as metal, ceramic, glass, or other material. Ferrules embodying features of the invention typically comprise substantially cylindrical portions, or portions comprising cylindrical shapes having channels introduced into a cylindrical shape. The cylindrical portions of ferrules and hypotubes embodying features of the invention typically have diameters of between about 0.001 inch and about 0.03 inch. In some embodiments, ferrule diameters may be between about 0.001 inch and about 0.01 inch, and in further embodiments, cylindrical portions of ferrules embodying features of the invention may comprise diameters of between about 0.001 inch and about 0.006 inch.

Hypotubes embodying features of the invention may be made of any suitable material, including but not limited to stainless steel, nickel titanium alloy, tantalum, and combinations of these materials. A radiopaque marking 31, or multiple radiopaque markings 31, may be placed on the OGW, such as, e.g., on a distal portion 19, on a proximal portion 38, or other position. Radiopaque markings 31 may comprise gold, tungsten, silver, platinum, alloys and mixtures of these metals, or other biocompatible radiopaque material. A radiopaque marker 31 or markers 31 may comprise bands, bars, dots, a mesh, or other shape or configuration compatible with incorporation into or placement on a guidewire.

OGWs embodying features of the invention may have tip coils or other features configured to aid in the insertion and positioning of the instruments. Such coils or other features located on a distal portion of an OGW embodying features of the invention may serve to enhance the ability of the guidewires to be guided to a desired location within a body lumen, and to enhance their ability to serve as a guiding rail for other instruments for placement of such other instruments in a desired location within a body lumen.

In addition, a guidewire for use with clinical optical imaging instrumentation must be suitable for sterilization. Thus, a rotatable ferrule as well as other portions of an OGW must be suitable for sterilization. Metals, such as stainless steel, nickel titanium alloy, tantalum, and other metals, are suitable for sterilization. Radiation sterilization, including electron-beam sterilization, is a common method of sterilization. Ceramics, polymeric materials and glasses are suitable for electron-beam sterilization. FEP is a suitable material that is more resistant to degradation by electron-beam sterilization than other polymeric materials. Accordingly, hypotubes and rotatable ferrules comprising metals, ceramic, glasses and polymeric materials, including FEP, are suitable for radiation sterilization.

A SQD 14 may be made from any suitable materials, including at least one material that may be sterilized. Metals, plastics, polymers, ceramics, composites, and glasses may all be used to make SQDs embodying features of the invention. A SQD may include seals and other components made of natural or synthetic rubber, including latex, nitrile, neoprene, and silicon rubber.

The ferrules embodying features of the invention typically find use in applications comprising multiple rotations of the ferrule. However, it will be understood that such ferrules may find use where only a single rotation, or only an incomplete rotation is desired, such as rotation of the tip of a guidewire by less than 180°, or less than 90°, or other amounts less than 360°.

Ferrules and SQDs embodying features of the invention may be used with any guidewire or guidewire component configured to receive or emit optical radiation, or to otherwise carry optical radiation from one portion of the guidewire to another. Thus, the devices, systems and methods of the invention find use in such applications as imaging, spectroscopy, illumination, optical sensing, temperature sensing, photoactivation of drugs and compounds at an intraluminal location, photoablation, optical heating, and any other application making use of optical radiation. In embodiments of the invention, to aid in the efficient coupling of light into and out of the proximal end of the optical fiber or fiber optic cable, a lens or lens assembly is incorporated at the proximal end of the optical fiber or fiber optic cable, or at the end of the ferrule.

The systems, interfaces, optical guidewires and methods of the invention find use in clinical and diagnostic procedures comprising imaging of an internal lumen of a patient's body. Such imaging of an internal lumen of a patient's body typically includes insertion of an optical guidewire, imaging catheter, endoscope, or other intracorporeal imaging device within a patient's body, and movement of the imaging instrument to a desired position within the patient's body in order to obtain desired imaging information regarding the lumen or lumen environment.

While the invention has been discussed in terms of certain preferred embodiments, it should be understood that various modifications may be made without departing from the scope thereof. Moreover, although certain individual features of a particular embodiment of the invention may be discussed herein or shown in the drawings illustrating one embodiment and not other embodiments, it should be apparent that individual features of one embodiment may be combined with one or more features of another embodiment.

What is claimed is:

1. An elongated intracorporeal optical instrument, comprising:

a. an elongated shaft having a longitudinal axis and proximal and distal portions having ends, the proximal portion having a substantially constant outer diameter, an optical pathway configured for passing optical radiation, and an internal surface having a proximal portion and defining an internal chamber within the elongated shaft extending to the optical pathway;
b. an elongated optical fiber extending substantially a length of said internal chamber of said elongated shaft;
c. a ferrule directly connected to said optical fiber and having a distal portion with a diameter and an outer surface, a proximal portion with a substantially constant outer diameter and an outer surface, the outer diameter being substantially the same as the outer diameter of the elongated shaft proximal portion, and configured to have a first position in which said ferrule is secured to the elongated shaft and a second position in which the ferrule is released from the elongated shaft and is free to rotate around said longitudinal axis;
wherein said ferrule diameters are each less than about 0.01 inch.

2. An elongated intracorporeal optical instrument, comprising:

a. an elongated shaft having a longitudinal axis and proximal and distal portions having ends, the proximal portion having a substantially constant outer diameter, an optical pathway configured for passing optical radiation, and an internal surface having a proximal portion and defining an internal chamber within the elongated shaft extending to the optical pathway;
b. an elongated optical fiber extending substantially an entire length of said internal chamber of said elongated shaft; and
c. a ferrule directly connected to said optical fiber and having a distal portion with a diameter and an outer surface, a proximal portion with a substantially constant outer diameter and an outer surface, the outer diameter being substantially the same as the outer diameter of the elongated shaft proximal portion, and configured to have a first position in which said ferrule is secured to the elongated shaft and a second position in which the ferrule is released from the elongated shaft and is free to rotate around said longitudinal axis, wherein said ferrule diameters are each less than about 0.006 inch.

* * * * *